(12) United States Patent
Rossau et al.

(10) Patent No.: US 6,656,689 B2
(45) Date of Patent: *Dec. 2, 2003

(54) HYBRIDIZATION PROBES DERIVED FROM THE SPACER REGION BETWEEN THE 16S AND 23S RRNA GENES FOR THE DETECTION OF NON-VIRAL MICROORGANISMS

(75) Inventors: Rudi Rossau, Ekeren (BE); Hugo Van Heuverswyn, Laarne (BE)

(73) Assignee: N.V. Innogenetics S.A., Ghent (BE)

( * ) Notice: Subject to any disclaimer, the term of this patent is extended or adjusted under 35 U.S.C. 154(b) by 11 days.

This patent is subject to a terminal disclaimer.

(21) Appl. No.: 09/863,086

(22) Filed: May 22, 2001

(65) Prior Publication Data

US 2002/0048762 A1 Apr. 25, 2002

Related U.S. Application Data

(63) Continuation of application No. 09/312,520, filed on May 14, 1999, now Pat. No. 6,277,577, which is a continuation of application No. 08/635,761, filed on Apr. 22, 1996, now Pat. No. 5,945,282, which is a continuation of application No. 08/412,614, filed on Mar. 29, 1995, now Pat. No. 5,536,638, which is a continuation of application No. 07/965,394, filed as application No. PCT/EP91/00743 on Apr. 18, 1991, now abandoned.

(30) Foreign Application Priority Data

Apr. 18, 1990 (GB) ............................................. 90401054

(51) Int. Cl.⁷ ........................... C12Q 1/68; C12P 19/34; C07H 21/02; C07H 21/04
(52) U.S. Cl. ........................ 435/6; 435/91.2; 536/23.1; 536/24.32; 536/24.33; 536/24.1
(58) Field of Search ................. 435/6, 91.2; 536/24.32, 536/24.33, 23.1, 24.1

(56) References Cited

U.S. PATENT DOCUMENTS

| | | | | |
|---|---|---|---|---|
| 4,900,659 A | | 2/1990 | Lo et al. ......................... | 435/6 |
| 5,378,606 A | | 1/1995 | Stern et al. ..................... | 435/6 |
| 5,536,638 A | * | 7/1996 | Rossau et al. .................. | 435/6 |
| 5,928,864 A | | 7/1999 | Kohne ............................. | 435/6 |
| 5,945,282 A | * | 8/1999 | Rossau et al. .................. | 435/6 |
| 6,277,577 B1 | * | 8/2001 | Rossau et al. .................. | 435/6 |

FOREIGN PATENT DOCUMENTS

| | | |
|---|---|---|
| EP | 0307270 | 3/1989 |
| EP | 0337896 | 10/1989 |
| EP | 0395292 | 10/1990 |
| EP | 0452596 | 10/1991 |
| EP | 0525095 | 2/1993 |
| WO | WO9600298 | 1/1996 |
| WO | WO9619585 | 6/1996 |
| WO | 88/03857 | 6/1998 |

OTHER PUBLICATIONS

PCT/EP 91/00743 International Application /International Search Report.
Emery et al., "An Irregular Satellite Sequence is Found at the Termini of the Linear Extrachromosomal rDNA in *Dictyostelium discoideum*", *Cell*, 26:411–419 (1981).
W. E. Evans et al., "The Use of DNA Probes for Taxonomic Study of Dictyostelium Wild Isolates", *Chemical Abstracts*, 109:391–392, Abstract No. 89552w (1988): and.
W. E. Evans et al., "The Use of DNA Probes for Taxonomic Study of Dictyostelium Wild Isolates", *Genetics Soc. Am.*, 119:561–569 (1988).
Gordon et al., (1982), Theor. Appl. Genet. 61:373–384.
G. Hide et al., "The Identification of Trypanosoma brucei Subspecies Using Repetitive DNA Sequences", *Chemical Abstracts*, 112:217, Abstract No. 173511b (1990); and.
G. Hide et al., "The Identification of Trypanosoma brucei Subspecies Using Repetitive DNA Sequences", *Molecular and Biochemical Parasitology*, 39:213–226 (1990).
King and Schlessinger (1983), J. Biol. Chem. 258:1203–42.
Lund and Dahlberg (1977) Cell 11:247–262.
Morgan, E. A., "Nucleotide Sequence of a 16s–23s rRNA Intergenic Region of *Escherichia coli*," Accession X12420 of publication *Nuc. Acids Res.* (1988).
Ness et al., "Chromatin Structure along the Ribosomal DNA of Dictyostelium: Regional Differences and Changes Accompanying Cell Differentiation", *J. Mol. Biol.*, 166:361–381 (1983).
Ripjens et al. (1996), Appl. Environ. Microbiol. 62:1683–88.
Ripjens et al. (1996), Mol. Cell. Probes 9:423–432.
R. Rossau et al., "Specific *Neisseria gonorrhoeae* DNA–Probes Derived from Ribosomal RNA", *Chemical Abstracts*, 111:204, Abstract No. 72106x (1989); and.
R. Rossau et al., "Specific *Neisseria gonorrhoeae* DNA–Probes Derived from Ribosomal RNA", *J. Gen. Microbiol.*, 135:1735–1745 (1989).
R. Rossau et al. (1992), Mol. Cell. Probes 9:423–432.
R. K. Saiki, et al., "Genetic analysis of amplified DNA with immobilized sequence–specific oligonucleotide probes", *Proc. Natl. Acad. Sci.*, vol. 86: 6230–6234 (Aug. 1989).
Tomioka, N., et al., "Nucleotide Sequence of the 16S–23S Spacer Region in the rrnA Operon from a Blue–Green Alga, *Anacystis nidulans*," *Mol. gen Genet.* 193:427–429 (1984).

(List continued on next page.)

Primary Examiner—Carla J. Myers
(74) Attorney, Agent, or Firm—Merchant & Gould P.C.

(57) ABSTRACT

The invention relates to a probe consisting of at least about 15 nucleotides from the spacer region between rRNA genes of a non-viral organism, particularly prokaryotic organism and more particularly bacteria, and preferably from about 15 nucleotides to about the maximum number of nucleotides of the spacer region and more preferably from about 15 to about 100 nucleotides to be used for the detection of non-viral microorganisms.

16 Claims, 10 Drawing Sheets

OTHER PUBLICATIONS

Torres et al., "Species and Genus Specificity of the Intergenic Spacer (IGS) in the Ribosomal RNA Genes of Cucurbitaceae", *Chemical Abstracts*, 112:224–225, Abstract No. 93063s (1990).

Vaneechoutte et al. (1992) FEMS Microbiol. Lett. 93:227–234.

M. Verma et al., "Phylogenetic Implication of Heterogeneity of the Nontranscribed Spacer of Ribosomal DNA Repeating Unit in Various Neurospora and Related Fungal Species", *Biological Abstracts*, 83(11)AB–118, Abstract No. 104704 (1987); and.

M. Verma et al., "Phylogenetic Implication of Heterogeneity of the Nontranscribed Spacer of Ribosomal DNA Repeating Unit in Various Neurospora and Related Fungal Species", *Curr. Genet.*, 11:309–314 (1987).

Wawrousek and Hansen (1983), J. Biol. Chem., 258:291–298.

Saiki et al. Proceedings of the National Academy of Sciences. 86: 6230–6234.

Ulrich et al. Embo J. 3:361–364.

White et al. PCR Protocols: A Guide to Methods and Applications. Academic Press, New York, NY, pp. 315–322.

* cited by examiner

Fig. 1

```
AGAGAAAGAAGGGGCTTTAGGCATTCACACTTATCGGTAAACTGAAAAGA    -50
::::::::::::::::::::::::::::::::::::::::::::::::::
AGAGAAAGAAGGGGCTTTAGGCATTCACACTTATCGGTAAACTGAAAAGA    -50

TGCGGAAGAAGCTTGAGTGAAGGCAAGGTTCGCTTAAGAAGGGAAACCGG    -100
::::::::::::::::::::::::::::::::::::::::::::::::::
TGCGGAAGAAGCTTGAGTGAAGGCAAGGTTCGCTTAAGAAGGGAAACCGG    -100

GTTTGTAGCTCAGCTGGTTAGAGCACACGCTTGATAAGCGTGAGGTCGGA    -150
::::::::::::::::::::::::::::::::::::::::::: :::::: 
GTTTGTAGCTCAGCTGGTTAGAGCACACGCTTGATAAGCGTGGGGTCGGA    -150

GGTTCAAGTCCTCCCAGACCCACCAAGAACGGGGGCATAGCTCAGTTGGT    -200
::::::::::::::::::::::::::::::::::::::::::::::::::
GGTTCAAGTCCTCCCAGACCCACCAAGAACGGGGGCATAGCTCAGTTGGT    -200

AGAGCACCTGCTTTGCAAGCAGGGGGTCATCGGTTCGATCCCGTTTGCCT    -250
::::::::::::::::::::::::::::::::::::::::::::::::::
AGAGCACCTGCTTTGCAAGCAGGGGGTCATCGGTTCGATCCCGTTTGCCT    -250

CCACCAAAACTTTACAAATGAAAGCAAGTTTGCTGTTTTAGCAGCTTAT    -300
:::::::::::::::::::::::::::::::::::::::::::::::::
CCACCAAAACTTTACAAATGAAAGCAAGTTTGCTGTTTTAGCAGCTTAT    -300

TTTGATTTGCGAAGTAGAATAACGACGCATCGATC
:::::::::::::::::::::::::::::::::::
TTTGATTTGCGAAGTAGAATAACGACGCATCGATC
```

Fig. 2

```
AAGAGCTTGAGTGCTCGTGTCAAGTGTCCACGCTTATCGGTTGTTGTTAT  -50
::::::::::::::::::::::::::::::::::::::::::::::::::
AAGAGCTTGAGTGCTCGTGTCAAGTGTCCACGCTTATCGGTTGTTGTTAT  -50

ATAGCTGCTGGATCGGTGGCTGCTGATCCGAGAGAGAAAGGTTTCGCGGG  -100
::::::::::::::::::::::::::::::::::::::::::::::::::
ATAGCTGCTGGATCGGTGGCTGCTGATCCGAGAGAGAAAGGTTTCGCGGG  -100

TCTGTAGCTCAGTCGGTTAGAGCACCGTCTTGATAAGGCGGGGGTCGTTG  -150
::::::::::::::::::::::::::::::::::::::::::::::::::
TCTGTAGCTCAGTCGGTTAGAGCACCGTCTTGATAAGGCGGGGGTCGTTG  -150

GTTCGAATCCAACCAGACCCACCAAGGTTTCCTGAGAGGGAAATGGGGGT  -200
::::::::::::::::::::::::::::::::::::::::::::::::::
GTTCGAATCCAACCAGACCCACCAAGGTTTCCTGAGAGGGAAATGGGGGT  -200

GTAGCTCAGCTGGGAGAGCGCCTGCTTTGCAAGCAGGATGTCATCGGTTC  -250
::::::::::::::::::::::::::::::::::::::::::::::::::
GTAGCTCAGCTGGGAGAGCGCCTGCTTTGCAAGCAGGATGTCATCGGTTC  -250

GATCCCGTTCACCTCCACCAAAGCCTGTCCAGAGGATGGGTGTGGNNNG-  -299
:::::::::::::::::::: ::::  :::   ::  ::::::  : ::        :
GATCCCGTTCACCTCCACCAGAGCCCGTCTTGAAGATGGGAGCGGGTTGG  -300

------AGACCAG-AAGGCGAGAGAGCAACGTTAGTGCTGCGAGTCAGTG  -342
       :::::::  :::::::::::::::::::::::::::::::::::
CAGGCGAGACCAGGAAGGCGAGAGAGCAACGTTAGTGCTGCGAGTCAGTG  -350

TTAAGCGTTGGGTTTTGGCCGACAGCTATATATGTTCTTTAACAATTTGG  -392
::::::::::::::::::::::::::::::::::::::::::::::::::
TTAAGCGTTGGGTTTTGGCCGACAGCTATATATGTTCTTTAACAATTTGG  -400

AAGAAGCACAACGTAAAGTGTTCGTTTAGTAGTCGGCGCGAGTCGATGAA  -442
::::::::::::::::::::::::::::::::::::  ::::::::::::
AAGAAGCACAACGTAAAGTGTTCGTTTAGTAGTCGACGCGAGTCGATGAA  -450

GACGGATACGGGTTGTGATTGCATGATTTTGTTCCAAGTCTCAAGAACTG  -492
::::::::::::::::::::::::::::::::::::::::::::::::::
GACGGATACGGGTTGTGATTGCATGATTTTGTTCCAAGTCTCAAGAACTG  -500

GCTGGGCGGCCAAGCGTTTGGTCAGATGCTTTGAACTTATGAACGGCACA  -542
::::::::::::::::::::::::::::::::::::::::::::::::::
GCTGGGCGGCCAAGCGTTTGGTCAGATGCTTTGAACTTATGAACGGCACA  -550

AGCGCGAATGAACAGCACCTATAAGACTTTAGTGTTATAG  -582
::::::::::::::::::::::::::::::::::::::::
AGCGCGAATGAACAGCACCTATAAGACTTTAGTGTTATAG  -590
```

Fig. 3

```
AGAGAAAGAAGAGGCTTTAGGCATTCACACTTATCGGTAAACTGAAAAAG -50
::::::::::: :::::::::::::::::::::::::::::::::: :
AGAGAAAGAAGGGGCTTTAGGCATTCACACTTATCGGTAAACTGAAAA-G -49

ATGCGGAAGAAGCTTGAGTGAAGGCAAGATTCGCTTAAGAAGAGAATCCG -100
::::::::::::::::::::::::: ::::::::::::::: ::: :::
ATGCGGAAGAAGCTTGAGTGAAGGCAAGGTTCGCTTAAGAAGGGAAACCG -99

GGTTTGTAGCTCAGCTGGTTAGAGCACACGCTTGATAAGCGTGGGGTCGG -150
:::::::::::::::::::::::::::::::::::::::::::: ::::::
GGTTTGTAGCTCAGCTGGTTAGAGCACACGCTTGATAAGCGTGAGGTCGG -149

AGGTTCAAGTCCTCCCAGACCCACCAAGAACGGGGGGCATAGCTCAGTTG -200
::::::::::::::::::::::::::::::::::::: ::::::::::::
AGGTTCAAGTCCTCCCAGACCCACCAAGAACGGGGG-CATAGCTCAGTTG -198

GTAGAGCACCTGCTTTGCAAGCAGGGGGTCATCGGTTCGATCCCGTTTGC -250
::::::::::::::::::::::::::::::::::::::::::::::::::
GTAGAGCACCTGCTTTGCAAGCAGGGGGTCATCGGTTCGATCCCGTTTGC -248

CTCCACCAATACTGTACAAATCAAAACGGAAGAATGGAACAGAATCCATT -300
::::::::: ::: ::::::::: ::: : ::: :: 
CTCCACCAAAACTTTACAAATGAAAGC--AAG---------------TT -280

CAGGGCGACGTCACACTTGACCAAGAACAAAATGCTGATATAATAATCAG -350
                                :::::: : :  :::
-----------------------------------TGCTGTTTTTAG---CAG -295

CTCGTTTTGATTTGCACAGTAGATAGCAATATCGAACGCATCGATCTTTA -400
::  :::::::::::: :::::: ::: :::  :::::::::::
CTTATTTTGATTTGCGAAGTAGA-----ATAACGA-CGCATCGATCTTTA -339

ACAAATTGGAAAGCCGAAATCAACAAACAAAGACAAAGCGTTTGTTTTGA -450
:::::::::::::::::::::::::::::::::::: : :::::::::::
ACAAATTGGAAAGCCGAAATCAACAAACAAAGACAATGAGTTTGTTTTGA -389

TTTTTTATTCTTTGCAAAGGATAAAAAATCGCTCACAAGAGAAAGAAAA -500
:::::::::::::::::::::::::::::: ::: :::::::::::::::
TTTTTTATTCTTTGCAAAGGATAAAAAATCTCTCGCAAGAGAAAGAAAA -439

CAAACACAGTATTTGGGTGATGATTGTATCGACTTAACCCTGAAACACAA -550
::::::  :::::::::::::::::::::::::::: :::::::::::::
CAAACATAGTATTTGGGTGATGATTGTATCGACTTAATCCTGAAACACAA -489

AAGGCAGGATTAAGACACAACAAAGCAGTAAGCTTTATCAAAGTAGGAAA -600
:::::::::::::::::::::::::::::::::::::::::::::::: :
AAGGCAGGATTAAGACACAACAAAGCAGTAAGCTTTATCAAAGTAGGGAT -539

TTCAAGTCTGATGTTCTAGTCAACGGAATGTTAGGCAAAGTCAAAGAAGT -650
:::::::  :: :  ::::::::::  : :: : :::::::::::::::
TTCAAGTTTGCTTACTTAGTCAACGGGTAGGTAAACGAAGTCAAAGAAGT -589

TCTTGAAATGATAG -664
::::::::::::::
TCTTGAAATGATAG -603
```

Fig. 4

```
A-GAGAAAGAAGGGGCTTT--AGGCATTCACACTTATCGGTAAACTGAAA  -47
: :::      ::   :  : :    : :   :  : :::  :::::::::::    ::
AAGAGCTTGAGTGCTCGTGTCAAGTGTCCACGCTTATCGGT----TGTTG  -46

AGATGCGGAAGAAGCTTGAGTGAAGGCAAGGTTCGCTTAAGAAGGGAAAC  -97
 ::    :   :   :  :::    ::    : :  ::      ::::: ::    :
TTATATAGCTGCTGGATCGGTGGCTGCT-GATCCGAGAGAGAAAGGTTTC  -95

-CGGGTTTGTAGCTCAGCTGGTTAGAGCACACGCTTGATAAGCGTGAGGT  -146
 :::::  :::::::::::  ::::::::::::   :::::::::  :  :::
GCGGGTCTGTAGCTCAGTCGGTTAGAGCACCGTCTTGATAAGGCGGGGGT  -145

CGGAGGTTCAAGTCCTCCCAGACCCACCAAG---------------AACG  -181
::   :::::  :  :::   :::::::::::::::              :: :
CGTTGGTTCGAATCCAACCAGACCCACCAAGGTTTCCTGAGAGGGAAATG  -195

GGGGCATAGCTCAGTTGGTAGAGCACCTGCTTTGCAAGCAGGGGGTCATC  -231
::::    :::::::::  :::   :::::   :::::::::::::::::::    :::::::
GGGGTGTAGCTCAGCTGGGAGAGCGCCTGCTTTGCAAGCAGGATGTCATC  -245

GGTTCGATCCCGTTTGCCTCCACCAAAACTTTACAAATGAAAGCAAGTTT  -281
:::::::::::::::::   :::::::::::::::  :  :  :   :  :::     ::
GGTTCGATCCCGTTCACCTCCACCAAAGCCTGTCCAGAGGATGGGTGTGG  -295

GCTGTTTTTAGCAGCTTATTTTGATTTGCGAAGTAGAATAACGACGCATC  -331
      :   :: ::    :        ::    ::   :: ::    :    ::   ::
NNNGAGACCAGAAGGCGAGA--GA---GCAACGTT--AGTGCTGCGAGTC  -338

GATCTTTAACAAATTGGAAAGCCGAAATCAACAAACAAAGACAATGAGTT  -381
:   :: : :    ::::     :       : :::    : : :   :   :::
AGTGTTAAGCG--TTGG---GTTTTGGCCGACAGCTATATA---T--GTT  -378

TGTTTTGATTTTTTATTCTTTGCAAAGGATAAAAAATC-TCTCGCAAGAG  -430
 ::     ::  :::       :::  :  :::       ::    :  :  :    :
CTTTAACAATTTGGAAGAAGCACAACGTA-AAGTGTTCGTTTAGTAGTCG  -427

AAAAGAAAACAAACATA-GTATTTGGGTGATGATTGTATCGACTTAATCC  -479
  ::     :    : : ::   ::::     :::::::::: ::  :: ::      : :
GCGCGAGTCGATGAAGACGGATACGGGTTGTGATTGCAT-GATTTGTTC  -476

TGAAACACAAAAGGCAGGATTAAGACACAACAAAGCAGTAAGCTTTATCA  -529
 :  :::: :  :::::   :        :    :  ::::::  ::    :::
CAAGTCTCAAGAA-CTGGCTGG-G---CGGCCAAGC-GT----TTGGTCA  -516

AAGTAGGGATTTCAAGTTTGCTTACTTAGTCAA-CGGGTAGGTAAACGAA  -578
: :      : :::  :: ::     : :          :::  ::  :  :  :  :
GA-T---GCTTTGAACTTA--TGAACGGCACAAGCGCGAATGAACAGCAC  -560

GTCAAAGAAGTTCTTGAAATGATAG  -603
  :   ::::   ::    ::          :  ::::
CTATAAGACTTTAGTG---TTATAG  -582
```

Fig. 5

```
AC-----GAAG----TT-----AT-----CTGATTGGCAA---GAA----   -24
 :     ::::    ::     ::     :: :: :: ::   :::
AGAGAAAGAAGGGGCTTTAGGCATTCACACTTATCGGTAAACTGAAAAGA   -50

TCCACAACAAG-TTGTTCTTTGGTAAGAT--GTTTAA------AAAC-GG   -64
: :  :: ::: :::      :: :::  : : ::::      :::: ::
TGCGGAAGAAGCTTGAGTGAAGGCAAGGTTCGCTTAAGAAGGGAAACCGG   -100

GTCTATAGCTCAGTTGGTTAGAGCACCGTGTTGATAACGCGG-GGTCAT   -113
:: : :::::::::: :::::::::::::   ::::::: ::: : ::::
GTTTGTAGCTCAGCTGGTTAGAGCACACGCTTGATAA-GCGTGAGGTCGG   -149

AAGTTCAAGTCTTATTAGACCCACCATTTT-GGGGCCATAGCTCAGTTGG   -162
: ::::::::: :  ::::::::::   ::::  :::::::::::::::
AGGTTCAAGTCCTCCCAGACCCACCAAGAACGGGGGCATAGCTCAGTTGG   -199

TAGAGCGCCTGCCTTGCACGCAGGAGGTCAGGAGTTCGACTCTCCTTGGC   -212
:::::: :::::  ::::: ::::  ::::::   :::::::  : ::: :
TAGAGCACCTGCTTTGCAAGCAGGGGGTCATCGGTTCGATCCCGTTTGCC   -249

TCCACCAAGCAAGTTTAAACATCAAAGCATACATAAGCAATTTAAATAAG   -262
:::::::: ::  ::::  : :: :::::::      :  ::: : :::
TCCACCAA--AACTTTACAAATGAAAGCAAG--TTTGCTGTTTTTAGCAG   -295

ATTTCTTATTTATGCTTT-TATTTTATAAACTGA-CGAAGTTTATAACAT   -310
:: :: :: :::    ::  ::     ::  : ::: ::::: : ::
CTTATTTTGATTTGCGAAGTAGAATAACGACGCATCGATCTTTAACAAAT   -345

T----------ATTTAACAA-CATAGT--ATGAGTCTGGGTTAATTATTT   -347
:          : : ::::: :: ::   ::::::: ::  :: ::: :::
TGGAAAGCCGAAATCAACAAACAAAGACAATGAGTTTGTTTTGATTTTTT   -395

AAT---TCCAACAAATAATTAACCTGGTGTTTGT--ACCCAATACAAACA   -392
: :   : :::  ::::  :: ::   :     :  :: ::::::::
ATTCTTTGCAAAGGATAAAAAATCTCTCGCAAGAGAAAAGAAAACAAACA   -445

CCAAA-----------AAAGTAAAGAG--AA--CTGAATCAA-----GC-   -421
:                : :::  ::  ::  ::::: ::      ::
TAGTATTTGGGTGATGATTGTATCGACTTAATCCTGAAACACAAAGGCA   -495

GTA---------AACATAGGTG-AATCGTTA-CACATTACCCATA-CAC-   -458
: :         :::: ::   : :: : ::: ::  ::  ::  ::
GGATTAAGACACAACAAAGCAGTAAGCTTTATCAAAGTAGGGATTTCAAG   -545

-------AC-----CAAAGACTTCCTA---GAAGTCAGACTA---CTTGG   -490
       ::     ::: : :  ::  :::::::: :  :    ::::
TTTGCTTACTTAGTCAACGGGTAGGTAAACGAAGTCAAAGAAGTTCTTGA   -595

GGTTGTAT   -498
 :   ::
AATGATAG   -603
```

Fig. 6

```
C-----------------------------------------  -1
:
CTTAACCTTCGGGAGGGCGCTTACCACTTTGTGATTCATGACTGGGGTGA  -50

--------CAAAATAA----AG----AC----------ATCAC-------  -18
        ::: :::     ::    ::          :::::
AGTCGTAACAAGGTAACCGTAGGGGAACCTGCGGTTGGATCACCTCCTTA  -100

-----AAGTA---------------CTCACACAGATTGTTTGATTGTTTT  -48
     ::: :               ::::::::::::::: :::: :
CCTTAAAGAAGCGTACTTTGTAGTGCTCACACAGATTGTCTGATAGAAAG  -150

AGA----CAAGTCG-----------------------------GAATA----  -63
::     :::: ::                             :::::
TGAAAAGCAAGGCGTTTACGCGTTGGGAGTGAGGCTGAAGAGAATAAGGC  -200

CAT---CTTT------------------------AAATGT-------  -76
: :   ::::                        :::: :
CGTTCGCTTTCTATTAATGAAAGCTCACCCTACACGAAAATATCACGCAA  -250

-------------------TGTCCCCATCTGTCTAGAGGCCTAGGACAT  -106
                   :::::::  :: :::::::::::: ::::::
CGCGTGATAAGCAATTTTCGTGTCCCCTTC-GTCTAGAGGCCCAGGACAC  -299

CGCCCTTTCACGGCGGTAACCGGGGTTCGAANCCCC--GTGGACGCCATC  -154
::::::::::::::::::::::: ::::::::::: ::::   : :::::::: :
CGCCCTTTCACGGCGGTAACAGGGGTTCGAATCCCCTAGGGGACGCCA-C  -348

TAAAGATGATTTTT-ATTGTCTTATGTT--CTTTAAAAAAATAGAAACAA  -201
:   : :: :::  : : ::         :     : :::: :    : ::    :
TT--GCTGGTTTGTGAGTGAAAGTCGCCGACCTTAATATCTCAAAACTCA  -396

GCT----GAAAACTGAGAGATTTTCTAAAGTAGAAAGTCTGAGT-AATCT  -246
::     :   :   :   :::::: ::        : ::: ::::  : :: ::
TCTTCGGGTGATGTTTGAGATNTTTGCTCTTTAAAAATCTGGATCAAGCT  -446

AAAATCTTAG---CTGAACAAAAGCAGCTAAGTGTTTAGTCTAAATCATT  -293
:::  : :   ::::::::   :: :       ::   :::::    :::
GAAAATTGAAACACTGAACAACGAGAGTTGTTCGTG-AGTCTCTCAAATT  -495

AACCACAAGTATATCAATATGCCTCGCGCATAATAAAATACTTGAGGTTG  -343
:   :::   ::    :::   :::            ::  :::   :::   :::::
TTCG-CAACACGAT---GATGAATCGA----AAGAAACATCTTCGGGTTG  -537

TAT  -346
:
TGA  -540
```

Fig. 7

```
ACGAAGTTATCTGATTGGCAAGAATCCACAACAAGTTGTTCTTTGGTAAG      -50
::::  ::::::::::::::::::::::::::::::::::::::::: : ::
ACGAGATTATCTGATTGGCAAGAATCCACAACAAGTTGTTCTTAG-TAGT      -49

ATGTTTAAAAACGGGTCTATAGCTCAGTTGGTTAGAGCACCGTGTTGATA      -100
 :   : :::  ::::::::::::::::::::::::::::::::  ::::::
GTAAGTTAAATTGGGTCTATAGCTCAGTTGGTTAGAGCACCGCCTTGATA      -99

ACGCGGGGGTCATAAGTTCAAGTCTTATTAGACCCACCATTTTGGGGCCA      -150
: :::::::::::::::::::::::::::::::::::::::::::::::  :
AGGCGGGGGTCATAAGTTCAAGTCTTATTAGACCCACCATTTTGGGGTTA      -149

TAGCTCAGTTGGTAGAGCGCCTGCCTTGCACGCAGGAGGTCAGGAGTTCG      -200
::::::::::::::::::::::::::::::::::::::::::::::::::
TAGCTCAGTTGGTAGAGCGCCTGCCTTGCACGCAGGAGGTCAGGAGTTCG      -199

ACTCTCCTTGGCTCCACCAAGCAAGTTTAA--ACATCAAAGCATACATAA      -248
:::::::::  ::::::::  :   : ::   : : :  :::::  ::  :
ACTCTCCTTAACTCCACCACTTACAATAAATGAGAACTAAGCAATCAAAT      -249

GCAAT----TTAAATAAGATTTCTTATTTATGCTTT---TATTTTA--TA      -289
 ::    :  ::::  :::::::::: ::  : ::::   ::  :  ::
TAGATAACATAAAATTAGATTTCTTACTTCTACTTTATGTAGATGACTTA      -299

-----AACTGACGAAGTTTATAACA-TTATTTAACAACATAG-TATGAGT      -332
     ::::::  ::::::::: ::  ::  :::::::::::  ::::::::
CAATTAACTGATGAAGTTAATTTCAATTATTTAACAACGTATATATGAGT      -349

CTGGGTTAATTATTTAATTCCAACAAATAATTAACCTGGTGTTTGTAC-C      -381
:::::::::::::::::::::::::::::::::::::    :  ::: :
CTGGGTTAATTATTTAATTCCAACAAATAATTAACCATTCCGTCATACTC      -399

CA--------ATACAAACACCAAA--------------------------A      -398
::         ::: :::   :::                          :
CACATCAAGCATATAAAGTTAAAACTTTTAGTATTGATGATGATCGGATA      -449

AAGTAAAGAGAACTGAATCAAGCGTAAACATAGGTGAATCGTTACACATT      -448
::::::::::::::::::::::::::::::::::::::::::::::::::
AAGTAAAGAGAACTGAATCAAGCGTAAACATAGGTGAATCGTTACACATT      -499

ACCCATACACACCAAAGACTTCCTAGAAGTCAGACTACTTGGGGTTGTAT      -498
::::::::::::::::::::::::::::::::::::::::::::::::::
ACCCATACACACCAAAGACTTCCTAGAAGTCAGACTACTTGGGGTTGTAT      -549
```

Fig. 8

```
CTGAAGACGAGAGACAGCGAGTGCTCACACAGATTGGCTGATAGTTGTAG   -50
:   ::::::::::::::::::::::::::::::::::::::::::::::
CCCAAGACGAGAGACAGCGAGTGCTCACACAGATTGGCTGATAGTTGTAG   -50

ACAAGATTAAAAACGAAGCGAAAGCAACGTTGAAAAATAAACGTTAAAAG  -100
::::::::::::::::::::::::::::::::::::::::::::::::::
ACAAGATTAAAAACGAAGCGAAAGCAACGTTGAAAAATAAACGTTAAAAG  -100

ATAAAAAGAAAATAGAGTATCTTTAATTGATGTCCCCATCGTCTAGAGGC  -150
::::::::::::::::::::::::::::::::::::::::::::::::::
ATAAAAAGAAAATAGAGTATCTTTAATTGATGTCCCCATCGTCTAGAGGC  -150

CTAGGACATCGCCCTTTCACGGCGGTAACCGGGGTTCGAATCCCCGTGGG  -200
::::::::::::::::::::::::::::::::::::::::::::::::::
CTAGGACATCGCCCTTTCACGGCGGTAACCGGGGTTCGAATCCCCGTGGG  -200

ACGCCAATTAAAGATAACTTTATTAGATTGTCTTACTGTTCTTTAAATTT  -250
::::::        ::::::::::::::::::::::::::::::::::
ACGCCANNNNNNNNNNNNNNTTTATTAGATTGTCTTACTGTTCTTTAAAAAA -250

TTGGAAACAAGCTGAAAACAAGAGATTTTCGAGAGAAAGTCTGAGTAGGC  -300
::::::::::::::::::::::::::::::::::::::::::::::::::
TTGGAAACAAGCTGAAAACAAGAGATTTTCGAGAGAAAGTCTGAGTAGGC  -300

AAGATAGGAAAGTGAGAGGAGGGAACTGAAAAGGGAACTCTAAAAACAAA  -350
::::  :::::::::: :  ::::::::::::   ::::::::::::::
AAGACAGGAAAGTGAAAAGAGGGAACTGAGAAGGAAACTCTAAAAACAAA  -350

ACCTGTTTTGCATAAAA-TCTTGATTGAACAAAAGCAATCAAGTGTTTAG  -399
::::::::: :  ::::  :::::::::::::::::  ::::::::::::
-CCTGTTTTGTAAAAAAATCTTGATTGAACAAAAGTAATCAAGTGTTTAG  -399

TTGAATGAAAATACGCATCAAATTGACCGCACTTTGAAGTGAAAACTTAA  -449
::::::  ::   :   :::  ::     ::   :   ::    :  ::  :
TTGAATTAA--TGAGGCTGAAAGTGCAGTCAAAGTACGGTATCTATTTTA  -447

-AGTGA---TTGAAAACATTTGAGGTGAT  -474
 : :::       ::::::::::::::
TATTGAGTTTTGAAAACATTTGANNNNNN  -476
```

Fig. 9

```
AAGGATAAGGAA--CTGCGCATTG-GTCTTGTTTAGTCTTGAGAGGTCTT  -47
::::::::::::  ::::      :::  ::::::::::::  ::::::::::::::
AAGGATAAGGAAACCTGCCATTTGCGTCTTGTTTAGTTTTGAGAGGTCTT  -50

GTGGGGCCTTAGCTCAGCTGGGAGAGCGCCTGCTTTGCACGCAGGAGGTC  -97
::::::::::::::::::::::::::::::::::::::::::::::::::
GTGGGGCCTTAGCTCAGCTGGGAGAGCGCCTGCTTTGCACGCAGGAGGTC  -100

AGCGGTTCGATCCCGCTAGGCTCCATTGGTGAGAGATCACCAAGTAATGC  -147
:::::::::::::::::::::::::::       ::  :    :::  :    ::
AGCGGTTCGATCCCGCTAGGCTCCATTGAATCGAAAGGTTCAAAT--TGT  -148

ACATTGAAAATTGAATATCTATATCAAAT---------------------  -176
:::::::::::::::::::::::::::::
TCATTGAAAATTGAATATCTATATCAAATTCCACGATCTAGAAATAGATT  -198

------AGTAACAAGAAAATAAACCGAAAACGCTGT-AGTATT-AATAAG  -218
      ::::::::::::::::::::::::::::::: : :::: ::: ::
GTAGAAAGTAACAAGAAAATAAACCGAAAACGCTGTGAATATTTAATGAG  -248

AGTTTATGACTGAAAGG---TCAGAAAATAA  -246
::   :   : ::::       :   :    :::::
TTTTCTAGTTTTAAAGAAACTAGGTTAATAA  -279
```

Fig. 10

```
TAAAATCTAAAGCAAGTATATAAAGTAGATTAAATATAAAATACAAACTC  -50
::::::::::::::::::::::::::::::::::::::::::::::::::
TAAAATCTAAAGCAAGTATATAAAGTAGATTAAATATAAAATACAAACTC  -50

TATACTTAGATTTATTTTTATCTTTAACTATAAAAGAATATACTTTAATA  -100
::::::::::::::::::::::::::::::::::::::::::::::::::
TATACTTAGATTTATTTTTATCTTTAACTATAAAAGAATATACTTTAATA  -100

AATATAAATAACATATACATTATGTATTTATATTTATAATGAGATTATTT  -150
::::::::::::::::::::::::::::::::::::::::::::::::::
AATATAAATAACATATACATTATGTATTTATATTTATAATGAGATTATTT  -150

AATATATATGCTTCCTTTAGGTTTTAAACCTAAATGTTCTTTTTAATTAT  -200
::::::::::::::::::::::::::::::::::::::::::::::::::
AATATATATGCTTCCTTTAGGTTTTAAACCTAAATGTTCTTTTTAATTAT  -200

CATTGTTAAGAGTCACAAGCAAGTTTTAATAAAAACAATTTTACAGGACT  -250
::::::::::::::::::::::::::::::::::::::::::::::::::
CATTGTTAAGAGTCACAAGCAAGTTTTAATAAAAACAATTTTACAGGACT  -250

TGTTAAAGGATAAAACCTATTTATCTTTTCTTTGGTTTAACTTATATCTT  -300
::::::::::::::::::::::::::::::::::::::::::::::::::
TGTTAAAGGATAAAACCTATTTATCTTTTCTTTGGTTTAACTTATATCTT  -300

TTAATTATCTTTATTTCTATAATAAAGAGAATATTAGATTTAAGATTTAT  -350
::::::::::::::::::::::::::::::::::::::::::::::::::
TTAATTATCTTTATTTCTATAATAAAGAGAATATTAGATTTAAGATTTAT  -350

AAATTAAAGACAAGTTTCAAACTCACAGCTTAGTTGAGACTAAATCATTT  -400
::::::::::::::::::::::::::::::::::::::::::::::::::
AAATTAAAGACAAGTTTCAAACTCACAGCTTAGTTGAGACTAAATCATTT  -400

AGTTTTATATTAAGTGTTTGAATGCTTTCCGTCTTAAGATAAAGAAGTCT  -450
::::::::::::::::::::::::::::::::::::::::::::::::::
AGTTTTATATTAAGTGTTTGAATGCTTTCCGTCTTAAGATAAAGAAGTCT  -450

TATCATAAAAACTTTAACAAGGAAGTGATGCGTTTTAGAATCAATAATAA  -500
::::::::::::::::::::::::::::::::::::::::::::::::::
TATCATAAAAACTTTAACAAGGAAGTGATGCGTTTTAGAATCAATAATAA  -500

AAGGTAAAAAA  -511
:::::::::::
AAGGTAAAAAA  -511
```

HYBRIDIZATION PROBES DERIVED FROM THE SPACER REGION BETWEEN THE 16S AND 23S RRNA GENES FOR THE DETECTION OF NON-VIRAL MICROORGANISMS

This application is a Continuation of application Ser. No. 09/312,520, filed May 14, 1999, now U.S. Pat. No. 6,277,577 which is a Continuation of application Ser. No. 08/635,761, filed Apr. 22, 1996, now U.S. Pat. No. 5,945,282 which is a Continuation of application Ser. No. 08/412,614, filed Mar. 29, 1995, now issued U.S. Pat. No. 5,536,638, which is a File Wrapper Continuation of application Ser. No. 07/965,394, filed Dec. 17, 1992, now abandoned, which was the national stage of international application PCT/EP91/00743 filed Apr. 18, 1999, which applications are incorporated herein by reference.

The invention relates to nucleic acid probes derived from the spacer region between the ribosomal ribonucleic acid (rRNA) gene, particularly between the 16S and 23S rRNA genes, to be used for the specific detection of non-viral organisms in a biological sample by a hybridization procedure.

Although much progress has been made in the last decade, for many microorganisms the diagnostic procedures currently in use are still laborious, nonsensitive and a specific. Many of these pitfalls can be overcome by using nucleic acid probes. These nucleic acid probes can, for instance, be total genomic deoxyribonucleic acid (DNA), plasmids, riboprobes or synthetic oligonucleotides and these probes may target the genomic DNA or messenger or stable RNA species present in biological samples. Although not necessary, the use of synthetic oligonucleotides is preferred. Oligonucleotides can be rapidly synthesized in large amounts using chemical methods, have a long shelf-life, and are easily purified and labeled.

For a reliable diagnosis of microorganisms using DNA-probe technology the probes used should be highly specific (i.e. they should not cross-react with nucleic acids from other organisms) and highly sensitive (i.e. most, if not all, strains of the organism to be detected should react with the probe). Hence, the preferred target sequences should have the following characteristics:

(i) The sequence should be present in the genome of each strain of the organism concerned.

(ii) The evolutionary diversity of the sequence should be such that, on the one hand, there is sufficient sequence-diversity to allow differentiation of the species concerned from other closely related species and, on the other hand, sufficient sequence-conservation to allow the detection of all strains of the species concerned with the probe used.

Species-specific probes have been described for a large number of organism. For a recent review see Tenover, Clin. Microbiol. Rev. 1:82–101, 1988.

However, it is not obvious from which gene in the genome that specific probe sequences can be derived. In probe development often large selection procedures have to be followed to obtain fragments which at last turn out to be specific for the organism under investigation (Korolik et al., J. Gen. Microbiol. 134:521–529, 1988; Grimont et al., J. Clin. Microbiol. 21:431–437, 1985; Welcher et al., Nucl. Acids Res. 14:10027–10044, 1986; Donegan et al., Mol. Cell. Probes 3:13–26, 1989; Beaulieu and ROY, Abstract nr D249, Abstracts of the Annual Meeting of the American Society for Microbiology, 1989). Most often the function or identity of the gene from which the specific fragment derives is not known and the screening procedure has to be blindly repeated each time another specific probe is wanted. The precise identification of a gene which meets the criteria listed above and which is ubiquitously present would obviate the need for time-consuming and tedious selections.

The 16S or 23S rRNA genes are quite often used for probe development since sequences can easily be obtained using described methods and it is known that variable regions exist within these highly conserved genes which can be used for species-specific detection. However, for certain organisms it may not be possible to derive highly specific and sensitive probes from the 16S and 23S rRNA genes, for instance, because their evolutionary nucleic acid sequence conservation is too high. Another consequence of the conserved character of these genes is that the differentiation of two organisms is often based on one or a few mismatches only in the target sequence which puts constraints on the stringency of the hybridization. A slight deviation from these conditions may result in misidentification.

Therefore the characterization of a ubiquitous gene which allows the development of species-specific probes for most organisms including those for which it was not possible to infer specific probes from the 16S and 23S rRNA genes, and which preferably have a broader stringency-range, would be extremely advantageous.

Each cellular organism possesses ribosomal RNA cistrons since its transcripts are essential for the function of ribosomes and the synthesis of proteins. In general the genes are present in multiple copies in the genome. In eubacteria the 16S rRNA gene [also called small subunit rRNA (srRNA)] is found at the 5' end of the rRNA cistron, followed by the 23S rRNA [also called large subunit rRNA(lrRNA)]. The 5S rRNA gene is located at the 3' end of the cistron. The 16S, 23S and 5S genes are separated by spacer regions in which transfer RNA (tRNA) genes and signal sequences involved in post-transcriptional processing may be found. At first the rRNA cistron is transcribed as one precursor RNA molecule. This primary transcript is further processed by endo- and exoribonucleases to its mature products. As a consequence, spacer region sequences are not exclusively present in the genome of the organism but also in precursor RNA molecules and processing products. The structure and processing of eubacterial rRNA cistrons is discussed in detail in the following reference: Gegenheimer and Apirion, Microbiol. Rev. 45:502–541, 1981.

The situation in nuclear genomes of eukaryotes somewhat differs in that a 5.8S RNA gene is located between the srRNA and lrRNA and 5S rRNA genes are arranged in separate long tandem arrays (Perry, Annu. Rev. Biochem. 45:605–629, 1976; Long and Dawid, Annu. Rev. Biochem. 49:727–764, 1980.). However, rRNA cistrons in the mitochondria or chloroplasts of eukaryotic organisms are prokaryotic in nature (Borst and Grivell, Nature 290:443–444, 1981).

The nucleic acid sequence of the spacer region of only a very limited number of eukaryotic or prokaryotic organisms is available from the literature (e.g. Young et al., J. Biol. Chem. 254:3264–3271, 1979; and Martens et al., System. Appl. Microbiol. 9:224–230, 1987.). From these data no reliable estimation of the nucleic acid sequence conservation can be made and consequently nothing can be concluded concerning the suitability of the spacer region for the selection of specific probes.

More precisely, concerning prokaryotes, hybridization probes derived from the spacer region between the 16S and 23S rRNA genes for the detection of microorganisms in a biological sample have not yet been described. Neither are they known for the corresponding spacer region between the small and large subunit rRNA genes of eukaryotes.

As far as eukaryotes are concerned, the use of a cloned fragment from a ribosomal gene spacer has been described in a taxonomical study on Leishmania (Ramirez and Guevara, Mol. Bioch. Parasitol. 22:177–183, 1987). However, the region used as well as the approach of the study are of no help to the man skilled in the art, for using a probe derived from the spacer region between the small rRNA and large rRNA genes, particularly for the following reasons:

(i) the ribosomal genes spacer used by Ramirez and Guevara is not the spacer region between the srRNA and lrRNA, but refers to the sequence present between two adjacent rRNA cistrons; such spacers are only found in eukaryotes between repeating units of rRNA cistrons and are not related to the internal spacer in between the srRNA and lrRNA genes;

(ii) the differentiation between *Leisbmania taxa* using the gene spacer fragment is achieved by comparing restriction fragment patterns; the fragment used is not specific.

Hence, differentiation with the fragment using a simple hybridization protocol without resorting to Southern blot analysis is not possible.

No evidence is presented that highly specific probes can be found in that ribosomal gene spacer.

Thus, the aim of the invention is to provide species-specific probes derived from the spacer region between rRNA genes for a particular organism such as a bacterial species.

Another object of the invention is to provide DNA probes derived from the 16S–23S rRNA spacer region for the detection of *Neisseria gonorrhoeae, Neisseria meningitidis, Branhamella catarrhalis, Haemophilus ducreyvi, Haemophilus influenzae, Bordetella pertussis, Streptococcus agalactiae, Streptococcus pneumoniae*, and *Campylobacter jejuni* and *Campylobacter coli* strains.

Still, another object of the invention is to provide DNA probes derived from the 16S–23S rRNA gene spacer region for the detection of *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae*, and *Campylobacter jejuni* and *Campylobacter coli* strains in a biological sample by a hybridization test such as a dot-spot, strand-displacement, competition, sandwich, or reversed hybridization test. Still another object of the invention is to provide probes and a simple method for the in vitro diagnosis of *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae*, and *Campylobacter jejuni* and *Campylobacter coli* strains.

The invention relates to a probe consisting of at least about 15 nucleotides of the spacer region between rRNA genes of a non-viral organism, particularly of a prokaryotic organism, and more particularly of a bacteria.

The invention relates more particularly to a probe consisting from about 15 nucleotides to about the maximum number of nucleotides of the spacer region, and more preferably from about 15 to about 100 nucleotides of the spacer region between the rRNA genes, particularly between 16S and 23S rRNA genes of a non-viral organism, particularly of prokaryotic organisms, and more particularly of bacteria.

In the following, the expression "spacer region" designates the spacer region between rRNA genes and more particularly between the 16S and 23S rRNA genes.

The invention relates to a probe for use in a hybridization assay, liable to be obtained in the process which comprises constructing an oligonucleotide that is sufficiently complementary to hybridize to a sequence of the spacer region between rRNA genes selected to be unique to non-viral organisms, particularly to prokaryotic organisms, more particularly to bacteria, which are to be detected with said sequence of the spacer region between rRNA genes being selected either by comparing the nucleotide sequence of the spacer region between the rRNA genes of the sought organism with the nucleotide sequence of the spacer region between the rRNA genes of the closest neighbours, selecting a sequence of about at least 15 nucleotides, and preferably from about 15 to about the maximum number of nucleotides of the spacer region and more preferably from about 15 to about 100 nucleotides, of the spacer region between rRNA genes of the sought organism which presents at least one mismatch with the spacer region between the rRNA genes of at least one of the closest neighbours, or by deleting, in the spacer region of the organism to be sought, the tRNA genes and possibly the signal sequences, to obtain a shortened spacer region and determining by trial and error a specific nucleotide sequence of at least about 15 nucleotides, and preferably from about 15 to about the maximum number of nucleotides of the spacer region and more preferably from about 15 to about 100 nucleotides, from the shortened spacer region, said sequence being able to hybridize specifically with the nucleic acids (DNA and/or RNAs) of the sought organism.

The invention relates particularly to a probe wherein the spacer region between rRNA genes is the transcribed spacer region between the 16S rRNA gene and the 23S rRNA gene.

The spacer regions of several microorganisms were cloned, sequenced and compared as will be outlined later herein. The comparison revealed that the nucleic acid sequence of the spacer region is of a semi-conserved nature, as compared with that of rRNA genes, which are highly conserved. Hence, the spacer region might be better suited for probe development than the rRNA genes itself. FIGS. 1, 2, and 10 illustrate that there is a high degree of sequence homology between highly related organisms (such as highly related strains from the same genospecies). Somewhat more sequence variations were found between moderately related organisms as shown in FIGS. 3 and 7. A total lack of significant sequence homology (except for the tRNA sequences) could be demonstrated between distantly related species, as shown in FIGS. 4 to 6.

In the Table below, homology values (in % sequence homology) of 16S rRNA sequences of different strains (16S hom) are compared with the corresponding homology values of the spacer regions (spacer hom). The homology values (16S hom and spacer hom) were calculated using the PC Gene software supplied by Intelligentics Inc. and Genofit SA (release 6.01/Apr. 20, 1989). The total number of nucleotides compared is given between parentheses. The results clearly show that the spacer region is less conserved than the 16S rRNA molecule.

| strains compared | | 16S | Spacer |
|---|---|---|---|
| strain 1 | Strain 2 | hom | hom |
| N. gonorrhoeae NCTC 8375 | N. gonorrhoeae ITG 4367 | 99.9% (1434) | 100% (335) |
| B. pertussis ATCC 10380 | B. bronchiseptica NCTC 452 | 100% (417) | 98.1% (582) |
| N. gonorrhoeae NCTC 8375 | N. meningitidis NCTC 10025 | 99% (1452) | 93.5% (603) |
| B. catarrhalis ITG 4197 | N. nonliquefaciens ATCC 19975 | 97.9% (1244) | 87.1% (498) |
| B. pertussis ATCC 10380 | N. gonorrhoeae NCTC 8375 | 86.3% (998) | 58.4% (582) |
| B. catarrhalis ITG 4197 | N. gonorrhoeae NCTC 8375 | 83.8% (1485) | 68.1% (498) |
| H. ducreyi CIP 541 | E. coli | 88.3% (1498) | 67.1% (346) |

As a result, highly species-specific and sensitive probes could be inferred from the spacer region sequence of the relevant pathogenic species under study, i.e. *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae*, and *Campylobacter jejuni* and *Campylobacter coli* strains. Valuable probes could also be derived from the spacer region for the species *Neisseria meningitidis* and *Bordetella pertussis* for which highly specific probes could not be found in the 16S and/or 23S rRNA molecules. It is very likely that specific probes for other species than those described herein (e.g. other Campylobacter species, other Haemophilus species, Actinobacillus species, Bacteroides species, Chlamydia species, etc.) can be inferred from spacer region sequences as well.

The target of the probes derived from the transcribed spacer region between the 16S and 23S rRNA gene is the genomic DNA and the precursor RNA molecules present in the cells to be detected. The detection of the precursor RNA molecules is advantageous since these molecules are single-stranded and may be present in multiple copies. On the other hand, DNA molecules are much more refractory to enzymatical degradation than RNA molecules. Hence, DNA targeting is preferred when biological samples cannot be processed and/or stored adequately to prevent RNA degradation prior to hybridization.

Another particular advantage of probes derived from the 16S–23S rRNA transcribed spacer regions lies in target detection after enzymatical amplification using the polymerase chain reaction (PCR). The spacer region of many microorganisms can for instance be enzymatically amplified using the same primers allocated in a conserved region of the 3'-end and the 5'-end of the 16S and the 23S rRNA genes respectively. Taking advantage of the highly conserved character of the rRNA genes, spacer regions of many organisms can be amplified, if preferred simultaneously, using the same reagents and protocol and afterwards the amplified fragment can be detected using a probe which specifically targets the spacer region of the organism of interest. An advantageous method for the simultaneous and specific detection of simultaneously amplified fragments is the reversed hybridization.

Since the spacer region is flanked by conserved sequences, the cloning and sequencing of this region with the aid of the PCR technique is simple, and the same protocol can be applied to a great variety of organisms. Hence, the sequences of the spacer regions are obtained by enzymatical amplification of rRNA genes using conserved primers allocated in the 16S or 23S rRNA. Examples of basic primer pairs which can be used for the amplification of fragments spanning the spacer region are:

```
Primer pair 1: TGGCTCAGAT TGAACGCTGG CGGC (SEQ ID NO:99), and
               CCTTTCCCTC ACGGTACTGG T (SEQ ID NO:100)

Primer pair 2: TGGGTGAAGT CGTAACAAGG TA (SEQ ID NO:101), and
               CACGTCCTTC GTCGCCT (SEQ ID NO:102).
```

The amplified fragment can be cloned as such or as two sub-fragments after digestion with a restriction enzyme recognizing a unique restriction site. A strategy for cloning PCR products in M13 has been described by Medlin et al. (Gene 71:491–499, 1988).

The same strategy can be used for cloning in a plasmid vector. In this approach the basic primers are extended at their 5'-end with a nucleotide sequence comprising an unique restriction site, enabling directional cloning of the fragment. After cloning in a plasmid vector the spacer region can be sequenced using the dideoxy chain-termination method.

This approach is considerably less tedious and time-consuming than the conventional cloning procedures using genomic banks or selected restriction endonuclease fragments.

Although sequence information is more rapidly obtained when the sequencing reactions are performed directly on PCR fragments without cloning, the sequence information generated from cloned fragments is more accurate and complete. In contrast to PCR fragments, cloned gene fragments can easily be purified in large amounts, which results in clearly readable sequencing ladders. Since one mismatch in the probe sequence may result in useless probes, accuracy is highly preferred over speed when obtaining sequences.

Taking into account the ease of obtaining spacer sequences with the approach outlined above, nucleotide sequence comparison of the spacer region of the organism for which a probe is desired with the spacer region of the closest neighbour is the preferred way to infer specific probe sequences.

The closest neighbour means the taxon which is known to be most closely related in terms of DNA homology and which has to be differentiated from the organism of interest.

Depending on the taxonomical position of the organism of interest, the closest neighbour may be very highly related to the organism of interest, exhibiting more than 75% degree of binding, or may be rather distantly related showing no significant percentage of DNA homology. In the initial renaturation rate method the degree of binding values are insignificant below about 30%; in solid phase DNA:DNA hybridization methods, DNA homologies become insignificant between 10 to 20% degree of binding.

However, when the nucleotide sequences of the closest neighbours from which the organism of interest has to be differentiated are not available, the selection of the specific probes can be done by trial and error. In that case, for each particular organism a specific probe region, which may be located anywhere in the spacer region, has to be defined experimentally only few areas in the spacer regions, such as tRNA genes or signal sequences can, in certain instances, be excluded a priori as probe regions. However, since 16S–23S rRNA spacer regions in general are small—usually not longer than 900 bp—good probe sequences can be readily found without extensive screening.

By way of example, for a spacer region between the 16S and 23S rRNA gene of 700 bp, the "shortened" spacer region obtained by deleting the tRNA gene and the signal sequence can be of about 500 bp.

The term "a biological sample" as used herein refers to a specimen such as a clinical sample (pus, sputum, blood, urine, etc.), an environmental sample, bacterial colonies, contaminated or pure cultures, purified nucleic acid, etc. in which the target sequence of interest is sought.

"rRNA gene spacer region derived" as used herein refers to the fact that the probes concerned hybridize with sequences located in the spacer region between ribosomal RNA genes normally present in the genome or transcript RNA molecules, no matter whether said probes are themselves formed of DNA or RNA fragments, or whether they consist of cloned fragments (in the case of DNA) or of synthetic oligonucleotides.

A hybridization probe of the invention for detecting *Neisseria gonorrhoeae* strains contains:

either a sequence belonging to a nucleic acid selected from the following group of nucleic acids and which includes from 15 to the maximum number of nucleotides of the selected nucleic acid,

```
Group NGI1:

CGATGCGTCG TTATTCTACT TCGC (SEQ ID NO:1)            NGI1

GCGAAGTAGA ATAACGACGC ATCG (SEQ ID NO:2)            NGI1IC

GCGAAGUAGA AUAACGACGC AUCG (SEQ ID NO:3)            NGI1ICR

CGAUGCGUCG UUAUUCUACU UCGC (SEQ ID NO:4)            NGI1R

Group NGI2:

TTCGTTTACC TACCCGTTGA CTAAGTAAGC AAAC (SEQ ID NO:5) NGI2

GTTTGCTTAC TTAGTCAACG GGTAGGTAAA CGAA (SEQ ID NO:6) NGI2IC

GUUUGCUUAC UUAGUCAACG GGUAGGUAAA CGAA (SEQ ID NO:7) NGI2ICR

UUGGUUUACC UACCCGUUGA CUAAGUAAGC AAAC (SEQ ID NO:8) NGI2R
``` or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Neisseria meningitidis* strains contains:

either a sequence belonging to a nucleic acid selected from the following group of nucleic acids and which includes from 15 to the maximum number of nucleotides of the selected nucleic acid,

```
Group NMI1:

GGTCAAGTGT GACGTCGCCC TG (SEQ ID NO:9)              NMI1

CAGGGCGACG TCACACTTGA CC (SEQ ID NO:10)             NMI1IC

CAGGGCGACG UCACACUUGA CC (SEQ ID NO:11)             NMI1ICR

GGUCAAGUGU GACGUCGCCC UG (SEQ ID NO:12)             NMI1R
```

Group NMI2:

| | |
|---|---|
| GTTCTTGGTC AAGTGTGACG TC (SEQ ID NO:13) | NMI2 |
| GACGTCACAC TTGACCAAGA AC (SEQ ID NO:14) | NMI2IC |
| GACGUCACAC UUGACCAAGA AC (SEQ ID NO:15) | NMI2ICR |
| GUUCUUGGUC AAGUGUGACG UC (SEQ ID NO:16) | NMI2R |

Group NMI3:

| | |
|---|---|
| GCGTTCGTTA TAGCTATCTA CTGTGC (SEQ ID NO:17) | NMI3 |
| GCACAGTAGA TAGCTATAAC GAACGC (SEQ ID NO:18) | NMI3IC |
| GCACAGUAGA UAGCUAUAAC GAACGC (SEQ ID NO:19) | NMI3ICR |
| GCGUUCGUUA UAGCUAUCUA CUGUGC (SEQ ID NO:20) | NMI3R |

Group NMI4:

| | |
|---|---|
| TGCGTTCGAT ATTGCTATCT ACTGTGCA (SEQ ID NO:21) | NMI4 |
| TGCACAGTAG ATAGCAATAT CGAACGCA (SEQ ID NO:22) | NMI4IC |
| UGCACAGUAG AUAGCAAUAU CGAACGCA (SEQ ID NO:23) | NMI4ICR |
| UGCGUUCGAU AUUGCUAUCU ACUGUGCA (SEQ ID NO:24) | NMI4R |

Group NMI5:

| | |
|---|---|
| TTTTGTTCTTGGTCAAGTGTGACGTCGCCCTGAATGGATTCTGTTCCATT (SEQ ID NO:25) | NMI5 |
| AATGGAACAGAATCCATTCAGGGCGACGTCACACTTGACCAAGAACAAAA (SEQ ID NO:26) | NMI5IC |
| AAUGGAACAGAAUCCAUUCAGGGCGACGUCACACUUGACCAAGAACAAAA (SEQ ID NO:27) | NMI5ICR |
| UUUUGUUCUUGGUCAAGUGUGACGUCGCCCUGAAUGGAUUCUGUUCCAUU (SEQ ID NO:28) | NMI5R |

Group NMI6

| | |
|---|---|
| TTTGCCTAAC ATTCCGTTGA CTAGAACATC AGAC (SEQ ID NO:29) | NMI6 |
| GTCTGATGTT CTAGTCAACG GAATGTTAGG CAAA (SEQ ID NO:30) | NMI6IC |
| GUCUGAUGUU CUAGUCAACG GAAUGUUAGG CAAA (SEQ ID NO:31) | NMI6ICR |
| UUUGCCUAAC AUUCCGUUGA CUAGAACAUC AGAC (SEQ ID NO:32) | NMI6R | or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Branhamella catarrhalis* strains contains:
either a sequence belonging to a nucleic acid selected from the following group of nucleic acids and which includes from 15 to the maximum number of nucleotides of the selected nucleic acid, Group BCI1:

| | |
|---|---|
| TTAAACATCT TACCAAAG (SEQ ID NO:33) | BCI1 |
| CTTTGGTAAG ATGTTTAA (SEQ ID NO:34) | BCI1IC |
| CUUUGGUAAG AUGUUUAA (SEQ ID NO:35) | BCI1ICR |
| UUAAACAUCU UACCAAAG (SEQ ID NO:36) | BCI1R |

Group BCI2:

| | |
|---|---|
| TTGATGTTTA AACTTGCTTG GTGGA (SEQ ID NO:37) | BCI2 |
| TCCACCAAGC AAGTTTAAAC ATCAA (SEQ ID NO:38) | BCI2IC |
| UCCACCAAGC AAGUUUAAAC AUCAA (SEQ ID NO:39) | BCI2ICR |
| UUGAUGUUUA AACUUGCUUG GUGGA (SEQ ID NO:40) | BCI2R | or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Haemophilus ducreyi* strains contains:

either a sequence belonging to a nucleic acid selected from the following group of nucleic acids and which includes from 15 to the maximum number of nucleotides of the selected nucleic acid,

| | | |
|---|---|---|
| TTATTATGCG CGAGGCATAT TG | (SEQ ID NO:41) | HDI1 |
| CAATATGCCT CGCGCATAAT AA | (SEQ ID NO:42) | HDI1IC |
| CAAUAUGCCU CGCGCAUAAU AA | (SEQ ID NO:43) | HDI1ICR |
| UUAUUAUGCG CGAGGCAUAU UG | (SEQ ID NO:44) | HDI1R | or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Haemophilus influenzae* strains contains:

either a sequence belonging to a nucleic acid selected from the following group of nucleic acids and which includes from 15 to the maximum number of nucleotides of the selected nucleic acid, Group HII1:

| | | |
|---|---|---|
| ACGCATCAAA TTGACCGCAC TT | (SEQ ID NO:45) | HII1 |
| AAGTGCGGTC AATTTGATGC GT | (SEQ ID NO:46) | HII1IC |
| AAGUGCGGUC AAUUUGAUGC GU | (SEQ ID NO:47) | HII1ICR |
| ACGCAUCAAA UUGACCGCAC UU | (SEQ ID NO:48) | HII1R |

Group HII2:

| | | |
|---|---|---|
| ACTTTGAAGT GAAAACTTAA AG | (SEQ ID NO:49) | HII2 |
| CTTTAAGTTT TCACTTCAAA GT | (SEQ ID NO:50) | HII2IC |
| CUUUAAGUUU UCACUUCAAA GU | (SEQ ID NO:51) | HII2ICR |
| ACUUUGAAGU GAAAACUUAA AG | (SEQ ID NO:52) | HII2R | or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Bordetella pertussis* strains contains:

either a sequence belonging to a nucleic acid selected from the following group of nucleic acids and which includes from 15 to the maximum number of nucleotides of the selected nucleic acid, Group BPI1:

| | | |
|---|---|---|
| CCACACCCAT CCTCTGGACA GGCTT | (SEQ ID NO:53) | BPI1 |
| AAGCCTGTCC AGAGGATGGG TGTGG | (SEQ ID NO:54) | BPI1IC |
| AAGCCUGUCC AGAGGAUGGG UGUGG | (SEQ ID NO:55) | BPI1ICR |
| CCACACCCAU CCUCUGGACA GGCUU | (SEQ ID NO:56) | BPI1R | or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Streptococcus pneumoniae* strains contains:

either a sequence belonging to a nucleic acid selected from the following group of nucleic acids and which includes from 15 to the maximum number of nucleotides of the selected nucleic acid, Group SPI1:

| | | |
|---|---|---|
| GTGAGAGATC ACCAAGTAAT GCA | (SEQ ID NO:57) | SPI1 |
| TGCATTACTT GGTGATCTCT CAC | (SEQ ID NO:58) | SPI1IC |
| UGCAUUACUU GGUGAUCUCU CAC | (SEQ ID NO:59) | SPI1ICR |
| GUGAGAGAUC ACCAAGUAAU GCA | (SEQ ID NO:60) | SPI1R |

Group SPI2

| | | |
|---|---|---|
| AGGAACTGCG CATTGGTCTT | (SEQ ID NO:61) | SPI2 |
| AAGACCAATG CGCAGTTCCT | (SEQ ID NO:62) | SPI2IC |
| AAGACCAAUG CGCAGUUCCU | (SEQ ID NO:63) | SPI2ICR |
| AGGAACUGCG CAUUGGUCUU | (SEQ ID NO:64) | SPI2R |

Group SPI3

| | | |
|---|---|---|
| GAGTTTATGA CTGAAAGGTC AGAA | (SEQ ID NO:65) | SPI3 |
| TTCTGACCTT TCAGTCATAA ACTC | (SEQ ID NO:66) | SPI3IC |
| UUCUGACCUU UCAGUCAUAA ACUC | (SEQ ID NO:67) | SPI3ICR |
| GAGUUUAUGA CUGAAAGGUC AGAA | (SEQ ID NO:68) | SPI3R | or a variant sequence which differs from any of the preceding sequences
either by addition to or removal from any of their respective extremities of one or several nucleotides,
or changing within any of said sequences of one or more nucleotides,
or both,
yet provided that in any of the above circumstances said probe still hybridizes with the same RNA or DNA target as the corresponding unmodified sequence.

A hybridization probe of the invention for detecting *Streptococcus agalactiae* strains contains:

either a sequence belonging to a nucleic acid selected from the following group of nucleic acids and which includes from 15 to the maximum number of nucleotides of the selected nucleic acid,

```
Group SAI1:

AATCGAAAGG TTCAAATTGT T  (SEQ ID NO:69)         SAI1

AACAATTTGA ACCTTTCGAT T  (SEQ ID NO:70)         SAI1IC

AACAAUUUGA ACCUUUCGAU U  (SEQ ID NO:71)         SAI1ICR

AAUCGAAAGG UUCAAAUUGU U  (SEQ ID NO:72)         SAI1R

Group SAI2:

GGAAACCTGC CATTTGCGTC TT (SEQ ID NO:73)         SAI2

AAGACGCAAA TGGCAGGTTT CC (SEQ ID NO:74)         SAI2IC

AAGACGCAAA UGGCAGGUUU CC (SEQ ID NO:75)         SAI2ICR

GGAAACCUGC CAUUUGCGUC UU (SEQ ID NO:76)         SAI2R

Group SAI3:

TCCACGATCT AGAAATAGAT TGTAGAA (SEQ ID NO:77)    SAI3

TTCTACAATC TATTTCTAGA TCGTGGA (SEQ ID NO:78)    SAI3IC

UUCUACAAUC UAUUUCUAGA UCGUGGA (SEQ ID NO:79)    SAI3ICR

UCCACGAUCU AGAAAUAGAU UGUAGAA (SEQ ID NO:80)    SAI3R

Group SAI4:

TCTAGTTTTA AAGAAACTAG GTT (SEQ ID NO:81)        SAI4

AACCTAGTTT CTTTAAAACT AGA (SEQ ID NO:82)        SAI4IC

AACCUAGUUU CUUUAAAACU AGA (SEQ ID NO:83)        SAI4ICR

UCUAGUUUUA AAGAAACUAG GUU (SEQ ID NO:84)        SAI4R
``` or a variant sequence which differs from any of the preceding sequences
 either by addition to or removal from any of their respective extremities of one or several nucleotides,
 or changing within any of said sequences of one or more nucleotides,
 or both,
yet provided that in any of the above circumstances said probe still hybridizes with the same RNA or DNA target as the corresponding unmodified sequence.

The invention also relates to hybridization probes for detecting *Campylobacter jejuni* and *Campylobacter coli* strains containing a sequence from 15 to the maximum number of nucleotides derived from the 16S–23S rRNA spacer sequence shown in FIG. 10, or the corresponding one wherein T is replaced by U, or its complement, or the corresponding one wherein T is raplced by U, provided that the probes, at the appropriate conditions, hybridize specifically with DNA and/or RNA from *Campylobacter jejuni* and *Campylobacter coli*.

In the sequences given in groups NGI1, NGI2, NMI1, NMI2, NMI3, NMI4, NMI5, NMI6, BCI1, BCI2, HDI1, HII1, HII2, BPI1, SPI1, SPI2, SPI3, SAI1, SAI2, SAI3, and SAI4 the letters stand for the following nucleotides:
A: Adenylic residue
C: Cytidylic residue
G: Guanidylic residue
T: Thymidylic residue
U: Uracylic residue Under the expression "target" is meant a sequence complementary to any of the sequences of groups NGI1, NGI2, NMI1, NMI2, NMI3, NMI4, NMI5, NMI6, BCI1, BCI2, HDI1, HII1, HII2, BPI1, SPI1, SPI2, SPI3, SAI1, SAI2, SAI3, and SAI4 as previously defined herein.

In cases where the probe of the invention would comprise nucleic acid elongations on either side or both of said above defined sequences—e.g. nucleic acid fragments of cloning vector or linker fragments resulting from the cleavage of said probe out of said cloning vector—it is understood that such elongations should be selected such as to avoid the possibility that they could themselves hybridize with any other corresponding complementary nucleic acid sequence outside of the above target in a DNA of any micro-organism likely to be tested by the process of this invention as later defined. Such hybridization would be of a parasitical nature and reduce the specificity of the probe. Preferred probes consist of nucleic acid fragments formed from any of the sequences of the groups defined above, with said fragments containing from 15 to the maximum number of nucleotides of the relevant nucleic acid sequence.

It is understood that in the above nucleotide sequences (and in the other ones referred to hereafter), the left end of the formulae always corresponds to a 5' extremity and the right end to a 3' extremity of the sequence concerned.

When reference is further made therein to a "probe of group 'X'"—with 'X' from NGI1, NGI2, NMI1, NMI2, NMI3, NMI4, NMI5, NMI6, BCI1, BCI2, HDI1, HII1, HII2, BPI1, SPI1, SPI2, SPI3, SAI1, SAI2, SAI3, and SAI4—it should be understood that such probe has a sequence included in one of the nucleic acids belonging to that group as defined above or further defined hereafter.

It is also understood that the word "nucleotide" as used herein refers indistinctly to ribonucleotides and deoxyribonucleotides and modified nucleotides such as inosine unless otherwise specified. The expression "nucleotides" also encompasses those which further comprise modification groups, e.g. chemical modification groups which do not affect their hybridization capabilities fundamentally. Such modification groups aim, for instance, at facilitating their coupling, either directly or indirectly, with suitable markers or labels for the subsequent detection of the probes so marked or labeled particularly in their hybridization products with the relevant RNA or DNA strand, e.g. that or those initially contained in a biological sample together with other DNA(S) and/or RNA(s).

For instance, such modification groups are recognizable by antibodies which, in. turn, can be recognized specifically by other antibodies, carrying a suitable enzymatic or fluorescent or chemiluminescent label. Possible labeling procedures will further be exemplified later herein.

The invention also relates to probes having any of the sequences defined above and in which some nucleotides are different, provided that the different nucleotide(s) do(es) not alter the specificity of the probes defined above. Some probes may consist of one of the nucleic acids belonging to any of the groups which are set forth above or of part thereof, with said probes however including nucleotidic elongation on either sides thereof to the extent that such elongations do not alter the specificity of said probes with the genetic material of *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains.

The invention thus provides for probes which are either replicas (those designated by numbers followed by "IC" or "ICR") in terms of nucleotide sequence of sequences contained in the RNAs or DNAs of most *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* with occasionally a few insignificant differences in nucleotide sequences or formed of sequences, those designated by bare numbers or by numbers followed by "R", complementary to sequences included in the natural DNAs or RNAs of *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli.*

More particularly, it should be noted that the target sequences in the DNAs concerned consist in any of the following successive sequences present in most, if not all, *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains, subject to possible insignificant natural differences from one strain to another, whereby such natural differences are not likely to affect the hybridization specificity of the probes of this invention with such targets:

In the case of *Neisseria gonorrhoeae*
GCGAAGTAGA ATAACGACGC ATCG (SEQ ID NO:2)
GTTTGCTTAC TTAGTCAACG GGTAGGTAAA CGAA (SEQ ID NO:6)

In the case of *Neisseria meningitidis*
CAGGGCGACG TCACACTTGA CC (SEQ ID NO:10)
GACGTCACAC TTGACCAAGA AC (SEQ ID NO:14)
GCACAGTAGA TAGCTATAAC GAACGC (SEQ ID NO:18)
TGCACAGTAG ATAGCAATAT CGAACGCA (SEQ ID NO:22)
AATGGAACAGAATCCATTCAGGGCGACGTCACAC-TTGACCAAGAACAAAA (SEQ ID NO:26)
GTCTGATGTT CTAGTCAACG GAATGTTAGG CAAA (SEQ ID NO:30)

In the case of *Branhamella catarrhalis*
CTTTGCTAAG ATGTTTAA (SEQ ID NO:34)
TCCACCAAGC AAGTTTAAAC ATCAA (SEQ ID NO:38)

In the case of *Haemophilus ducreyi*
CAATATGCCT CGCGCATAAT AA (SEQ ID NO:42)

In the case of *Bordetella pertussis*
AAGCCTGTCC AGAGGATGGG TGTGG (SEQ ID NO:54)

In the case of *Haemophilus influenzae*
AAGTGCGGTC AATTTGATGC GT (SEQ ID NO:46)
CTTTAAGTTT TCACTTCAAA GT (SEQ ID NO:50)

In the case of *Streptococcus pneumoniae*
TGCATTACTT GGTGATCTCT CAC (SEQ ID NO:58)
AAGACCAATG CGCAGTTCCT (SEQ ID NO:62)
TTCTGACCTT TCAGTCATAA ACTC (SEQ ID NO:66)

In the case of *Streptococcus agalactiae*
AACAATTTGA ACCTTTCGAT T (SEQ ID NO:70)
AAGACGCAAA TGGCAGGTTT CC (SEQ ID NO:74)
TTCTACAATC TATTTCTAGA TCGTGGA (SEQ ID NO:78)
AACCTAGTTT CTTTAAAACT AGA (SEQ ID NO:82)

The probes according to the invention can be formed by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the invention can also be synthesized chemically, for instance by the conventional phospho-triester method.

The invention also relates to a process for detecting *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains in a biological sample, wherein said process comprises contacting said biological sample in which the nucleic acids (DNAs and RNAs) have been made accessible to hybridization, if need be under suitable denaturation conditions, with a probe of the invention under conditions enabling hybridization between the probe and complementary nucleic acids of the strains, which may be present in the sample, and detecting the hybrids possibly formed.

The process of the invention enables to discriminate *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* from most other organism such as yeast, fungi, protozoa, other bacterial strains, and/or human cells which are liable to the be present in the sample in which the organisms of interest are sought. The process relates to the detection of *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains being directly in the sample or after the strain has been cultured.

The detection of a hybrid can be interpreted as meaning that an infection due to *Neisseria gonorrhoeae, Neisseria meningitidis, Branhamella catarrhalis, Haemophilus ducreyi, Haemophilus influenzae, Bordetella pertussis, Streptococcus agalactiae,* and *Streptococcus pneumoniae* was present in the biological sample, when any of the probes of groups NGI1, NGI2, NMI1, NMI2, NMI3, NMI4, NMI5, NMI6, BCI1, BCI2, HDI1, HII1, HII2, BPI1, SPI1, SPI2, SPI3, SAI1, SAI2, SAI3, and SAI4 is being used, respectively.

According to an advantageous embodiment of the invention, in the process for detecting *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains, the probes used are the ones hybridizing both with DNA globally and RNA of the *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains, which may be present in the biological sample.

The hybridization conditions can be monitored relying upon several parameters, e.g. hybridization temperature, the nature and concentration of the components of the media, and the temperature under which the hybrids formed are washed.

The hybridization and wash temperature is limited in upper value, according to the probe (its nucleic acid composition, kind and length) and the maximum hybridization or wash temperature of the probes described herein is about 30° C. to 58° C. At higher temperatures duplexing competes with the dissociation (or denaturation) of the hybrid formed between the probe and the target.

A preferred hybridization medium contains about 3× SSC (1×SSC=0.15 M NaCl, 0.015 M sodium citrate, pH 7.0), about 25 mM of phosphate buffer pH 7.1, and 20% deionized formamide, 0.02% Ficoll, 0.02% bovine serum albumin, 0.02% polyvinylpyrrolidone and about 0.1 mg/ml sheared denatured salmon sperm DNA.

A preferred wash medium contains about 3×SSC, 25 mM phosphate buffer pH 7.1 and 20% deionized formamide. Other hybridization or wash media can be used as well.

However, when modifications are introduced, be it either in the probes or in the media, the temperatures at which the probes can be used to obtain the required specificity should be changed according to known relationships, such as those described in the following reference: B. D. HAMES and S. J. HIGGINS, (eds.). Nucleic acid hybridization. A practical approach, IRL Press, Oxford, U.K., 1985.

In this respect it should also be noted that, in general, DNA:DNA hybrids are less stable then RNA:DNA or RNA:RNA hybrids. Depending on the nature of the hybrid to be detected, the hybridization conditions should be adapted accordingly to achieve specific detection.

The process for detecting *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* strains generally, according to the invention can be carried out by suitably adjusting the hybridization temperature to a value at which hybridization is specific. In such a case, washing under more stringent conditions is not necessary.

According to another embodiment of the process of the invention, the hybridization temperature need not necessarily be adjusted to the value at which hybridization is specific and, in particular, can be lower than the temperature at which hybridization is specific, provided washing is carried out at a temperature corresponding to the value at which hybridization is specific.

In a process embodiment for detecting *Neisseria gonorrhoeae* strains (and for distinguishing them from other bacterial taxa) with a probe of group NGI1, the hybridization temperature and/or the wash temperature is suitably adjusted to about 50° C., the media being those defined above.

In a process embodiment for detecting *Neisseria gonorrhoeae* strains (and for distinguishing them from other bacterial taxa) with a probe of group NGI2, the hybridization temperature and/or the wash temperature is suitably adjusted to about 50° C., the media being those defined above.

In a process embodiment for detecting *Neisseria meningitidis* strains (and for distinguishing them from other bacterial taxa) with a probe of group NMI1, the hybridization temperature and/or the wash temperature is suitably adjusted to about 45° C., the media being those defined above.

In a process embodiment for detecting *Neisseria meningitidis* strains (and for distinguishing them from other bacterial taxa) with a probe of group NMI2, the hybridization temperature and/or the wash temperature is suitably adjusted to about 45° C., the media being those defined above.

In a process embodiment for detecting *Neisseria meningitidis* strains (and for distinguishing them from other bacterial taxa) with a probe of group NMI3, the hybridization temperature and/or the wash temperature is suitably adjusted to about 40° C., the media being those defined above.

In a process embodiment for detecting *Neisseria meningitidis* strains (and for distinguishing them from other bacterial taxa) with a probe of group NMI4, the hybridization temperature and/or the wash temperature is suitably adjusted to about 48° C., the media being those defined above.

In a process embodiment for detecting *Neisseria meningitidis* strains (and for distinguishing them from other bacterial taxa) with a probe of group NMI5, the hybridization temperature and/or the wash temperature is suitably adjusted to about 58° C., the media being those defined above.

In a process embodiment for detecting *Neisseria meningitidis* strains (and for distinguishing them from other bacterial taxa) with a probe of group NMI6, the hybridization temperature and/or the wash temperature is suitably adjusted to about 50° C., the media being those defined above.

In a process embodiment for detecting *Branhamella catarrhalis* strains (and for distinguishing them from other bacterial taxa) with a probe of group BCI1, the hybridization temperature and/or the wash temperature is suitably adjusted to about 30° C., the media being those defined above.

In a process embodiment for detecting *Branhamella catarrhalis* strains (and for distinguishing them from other bacterial taxa) with a probe of group BCI2, the hybridization temperature and/or the wash temperature is suitably adjusted to about 42° C., the media being those defined above.

In a process embodiment for detecting *Bordetella pertussis* strains (and for distinguishing them from other bacterial taxa) with a probe of group BPI1, the hybridization temperature and/or the wash temperature is suitably adjusted to about 55° C., the media being those defined above.

In a process embodiment for detecting *Haemophilus ducreyi* strains (and for distinguishing them from other bacterial taxa) with a probe of group HDI1, the hybridization temperature and/or the wash temperature is suitably adjusted to about 40° C., the media being those defined above.

In a process embodiment for detecting *Haemophilus influenzae* strains (and for distinguishing them from other bacterial taxa) with a probe of group HII1, the hybridization temperature and/or the wash temperature is suitably adjusted to about 55° C., the media being those defined above.

In a process embodiment for detecting *Haemophilus influenzae* strains (and for distinguishing them from other bacterial taxa) with a probe of group HII2, the hybridization temperature and/or the wash temperature is suitably adjusted to about 35° C., the media being those defined above.

In a process embodiment for detecting *Streptococcus agalactiae* strains (and for distinguishing them from other bacterial taxa) with a probe of group SAI1, the hybridization temperature and/or the wash temperature is suitably adjusted to about 35° C., the media being those defined above.

In a process embodiment for detecting *Streptococcus agalactiae* strains (and for distinguishing them from other bacterial taxa) with a probe of group SAI2, the hybridization temperature and/or the wash temperature is suitably adjusted to about 45° C., the media being those defined above.

In a process embodiment for detecting *Streptococcus agalactiae* strains (and for distinguishing them from other bacterial taxa) with a probe of group SAI3, the hybridization temperature and/or the wash temperature is suitably adjusted to about 45° C., the media being those defined above.

In a process embodiment for detecting *Streptococcus agalactiae* strains (and for distinguishing them from other bacterial taxa) with a probe of group SAI4, the hybridization temperature and/or the wash temperature is suitably adjusted to about 37° C., the media being those defined above.

In a process embodiment for detecting *Streptococcus pneumoniae* strains (and for distinguishing them from other bacterial taxa) with a probe of group SPI1, the hybridization temperature and/or the wash temperature is suitably adjusted to about 45° C., the media being those defined above.

In a process embodiment for detecting *Streptococcus pneumoniae* strains (and for distinguishing them from other bacterial taxa) with a probe of group SPI2, the hybridization temperature and/or the wash temperature is suitably adjusted to about 45° C., the media being those defined above.

In a process embodiment for detecting *Streptococcus pneumoniae* strains (and for distinguishing them from other bacterial taxa) with a probe of group SPI3, the hybridization temperature and/or the wash temperature is suitably adjusted to about 45° C., the media being those defined above.

The invention further relates to a kit for detecting specifically *Neisseria meningitidis* strains containing:
   a probe specific for *Neisseria meningitidis* i.e. a probe of group NMI1, NMI2, NMI3, NMI4, NMI5 or NMI6;
   the buffer or components necessary for producing the buffer enabling an hybridization reaction between these probes and only the DNAs and/or RNAs of a strain of *Neisseria meningitidis* to be carried out,
   the means for detecting the hybrids resulting from the proceeding hybridization, when appropriate.

The invention further relates to a kit for detecting specifically *Neisseria gonorrhoeae* strains containing:
   a probe specific for Neisseria gonorrhoeae i.e. a probe of group NGI1 or NGI2;
   the buffer or components necessary for producing the buffer enabling an hybridization reaction between these probes and only the DNAs and/or RNAs of a strain of *Neisseria gonorrhoeae* to be carried out,
   the means for detecting the hybrids resulting from the proceeding hybridization, when appropriate.

The invention further relates to a kit for detecting specifically *Branhamella catarrhalis* strains containing:
   at least one probe selected among any of those that are specific for *Branhamella catarrhalis* as above defined, i.e. a probe of group BCI1 or BCI2;
   the buffer or components necessary for producing the buffer enabling an hybridization reaction between these probes and only the DNAs and/or RNAs of a strain of *Branhamella catarrhalis* to be carried out,
   the means for detecting the hybrids resulting from the proceeding hybridization, when appropriate.

The invention further relates to a kit for detecting specifically *Haemophilus ducreyi* strains containing:
   at least one probe selected among any of those that are specific for *Haemophilus ducreyi* as above defined, i.e. a probe of group HDI1;
   the buffer or components necessary for producing the buffer enabling an hybridization reaction between these probes and only the DNAs and/or RNAs of a strain of *Haemophilus ducreyi* to be carried out,
   the means for detecting the hybrids resulting from the proceeding hybridization, when appropriate.

The invention further relates to a kit for detecting specifically *Bordetella pertussis* strains containing:
   at least one probe selected among any of those that are specific for *Bordetella pertussis* as above defined, i.e. a probe of group BPI1;
   the buffer or components necessary for producing the buffer enabling an hybridization reaction between these probes and only the DNAs and/or RNAs of a strain of *Bordetella pertussis* to be carried out,
   the means for detecting the hybrids resulting from the proceeding hybridization, when appropriate.

The invention further relates to a kit for detecting specifically *Haemophilus influenzae* strains containing:
   at least one probe selected among any of those that are specific for *Haemophilus influenzae* as above defined, i.e. a probe of group HIl1 or HIl2;
   the buffer or components necessary for producing the buffer enabling an hybridization reaction between these probes and only the DNAs and/or RNAs of a strain of *Haemophilus influenzae* to be carried out,
   the means for detecting the hybrids resulting from the proceeding hybridization, when appropriate.

The invention further relates to a kit for detecting specifically *Streptococcus agalactiae* strains containing:
   at least one probe selected among any of those that are specific for *Streptococcus agalactiae* as above defined, i.e. a probe of group SAI1, SAI2, SAI3, or SAI4;
   the buffer or components necessary for producing the buffer enabling an hybridization reaction between these probes and only the DNAs and/or RNAs of a strain of *Streptococcus agalactiae* to be carried out,
   the means for detecting the hybrids resulting from the proceeding hybridization, when appropriate.

The invention further relates to a kit for detecting specifically *Streptococcus pneumoniae* strains containing:
   at least one probe selected among any of those that are specific for *Streptococcus pneumoniae* as above defined, i.e. a probe of group SPI1, SPI2 or SPI3;
   the buffer or components necessary for producing the buffer enabling an hybridization reaction between these probes and only the DNAs and/or RNAs of a strain of *Streptococcus pneumoniae* to be carried out,
   the means for detecting the hybrids resulting from the proceeding hybridization, when appropriate.

The invention further relates to a kit for detecting specifically *Campylobacter jejuni* and *Campylobacter coli* strains containing:
   at least one probe selected among any of those that are specific for *Campylobacter jejuni* and *Campylobacter coli* as above defined;
   the buffer or components necessary for producing the buffer enabling an hybridization reaction between these probes and only the DNAs and/or RNAs of a strain of *Campylobacter jejuni* and *Campylobacter coli* to be carried out, the means for detecting the hybrids resulting from the proceeding hybridization, when appropriate.

The probes of the invention can be used in a sandwich hybridization system which enhances the specificity of a nucleic acid probe-based assay. The principle and the use of sandwich hybridizations in a nucleic acid probe-based assay have been already described (e.g.: DUNN and HASSEL, Cell, 12: 23–36; 1977; RANKI et al., Gene, 21: 77–85; 1983). Although direct hybridization assays have favorable kinetics, sandwich hybridizations are advantageous with respect to a higher signal-to-noise ratio. Moreover, sandwich hybridizations can enhance the specificity of a nucleic acid probe based assay.

If properly designed, a sandwich hybridization assay indeed maximizes the specificity of a nucleic acid probe-based test when using two probes recognizing two different nucleic acid stretches of one and the same organism. The only demands which must be met are that both probes (i) hybridize to the same nucleic acid molecule of the target organism and (ii) do not hybridize to the same non-target organisms.

For two given probes I and II, the sandwich hybridization system can be described as follows: Probe n· I hybridizes to nucleic acid from organisms A and B (not with C); Probe n· II hybridizes to nucleic acid from organisms A and C (not with B).

Since it is absolutely required that both probes hybridize to the target nucleic acid, a detectable signal will be generated only if the nucleic acid from organism A is present in the sample. It is obvious that if one of the probes is specific for the organism to be detected, the other probe can be composed of any specific or non-specific sequence provided that it hybridizes to the same target molecule than the first probe.

The probes of the invention can be used in a sandwich hybridization assay which is specific for *Neisseria gonorrhoeae, Neisseria meningitidis, Branhamella catarrhalis, Haemophilus ducreyi, Haemophilus influenzae, Bordetella pertussis, Streptococcus agalactiae, Streptococcus pneumoniae,* or *Campylobacter jejuni* and *Campylobacter coli* respectively in combination with another, non-specific or specific, probe hybridizing to the same target molecule. In the sandwich hybridization process, the probes can be added simultaneously or not, to the biological sample in which the target DNA or RNA is sought.

The invention also relates to a kit for sandwich hybridization assay, for the detection in vitro of *Neisseria gonorrhoeae* strains in a biological sample, with said kit containing:

at least two probes targeting the same nucleic acid molecule and of which at least one is specific for *Neisseria gonorrhoeae*, the buffer or components necessary for producing the buffer enabling hybridization reaction between these probes and the DNAs and/or RNAs of a strain of *Neisseria gonorrhoeae* to be carried out, the means for detecting the hybrids resulting from the preceding hybridization, when appropriate.

The invention also relates to a kit for sandwich hybridization assay, for the detection in vitro of *Neisseria meningitidis* strains in a biological sample, with said kit containing:

at least two probes targeting the same nucleic acid molecule and of which at least one is specific for *Neisseria meningitidis*, the buffer or components necessary for producing the buffer enabling hybridization reaction between these probes and the DNAs and/or RNAs of a strain of *Neisseria meningitidis* to be carried out, the means for detecting the hybrids resulting from the preceding hybridization, when appropriate.

The invention also relates to a kit for sandwich hybridization assay, for the detection in vitro of *Branhamella catarrhalis* strains in a biological sample, with said kit containing:

at least two probes targeting the same nucleic acid molecule and of which at least one is specific for *Branhamella catarrhalis*, the buffer or components necessary for producing the buffer enabling hybridization reaction between these probes and the DNAs and/or RNAs of a strain of *Branhamella catarrhalis* to be carried out, the means for detecting the hybrids resulting from the preceding hybridization, when appropriate.

The invention also relates to a kit for sandwich hybridization assay, for the detection in vitro of *Haemophilus ducreyi* strains in a biological sample, with said kit containing:

at least two probes targeting the same nucleic acid molecule and of which at least one is specific for *Haemophilus ducreyi*, the buffer or components necessary for producing the buffer enabling hybridization reaction between these probes and the DNAs and/or RNAs of a strain of *Haemophilus ducreyi* to be carried out, the means for detecting the hybrids resulting from the preceding hybridization, when appropriate.

The invention also relates to a kit for sandwich hybridization assay, for the detection in vitro of *Haemophilus influenzae* strains in a biological sample, with said kit containing:

at least two probes targeting the same nucleic acid molecule and of which at least one is specific for *Haemophilus influenzae*, the buffer or components necessary for producing the buffer enabling hybridization reaction between these probes and the DNAs and/or RNAs of a strain of *Haemophilus influenzae* to be carried out, the means for detecting the hybrids resulting from the preceding hybridization, when appropriate.

The invention also relates to a kit for sandwich hybridization assay, for the detection in vitro of *Bordetella pertussis* strains in a biological sample, with said kit containing:

at least two probes targeting the same nucleic acid molecule and of which at least one is specific for *Bordetella pertussis*, the buffer or components necessary for producing the buffer enabling hybridization reaction between these probes and the DNAs and/or RNAs of a strain of *Bordetella pertussis* to be carried out, the means for detecting the hybrids resulting from the preceding hybridization, when appropriate.

The invention also relates to a kit for sandwich hybridization assay, for the detection in vitro of *Streptococcus agalactiae* strains in a biological sample, with said kit containing:

at least two probes targeting the same nucleic acid molecule and of which at least one is specific for *Streptococcus agalactiae*, the buffer or components necessary for producing the buffer enabling hybridization reaction between these probes and the DNAs and/or RNAs of a strain of *Streptococcus agalactiae* to be carried out, the means for detecting the hybrids resulting from the preceding hybridization, when appropriate.

The invention also relates to a kit for sandwich hybridization assay, for the detection in vitro of *Streptococcus pneumoniae* strains in a biological sample, with said kit containing:

at least two probes targeting the same nucleic acid molecule and of which at least one is specific for *Streptococcus pneumoniae*, the buffer or components necessary for producing the buffer enabling hybridization reaction between these probes and the DNAs and/or RNAs of a strain of *Streptococcus pneumoniae* to be carried out, the means for detecting the hybrids resulting from the preceding hybridization, when appropriate.

The invention also relates to a kit for sandwich hybridization assay, for the detection in vitro of *Campylobacter jejuni* strains in a biological sample, with said kit containing:

at least two probes targeting the same nucleic acid molecule and of which at least one is specific for *Campylobacter jejuni*, the buffer or components necessary for producing the buffer enabling hybridization reaction between these probes and the DNAs and/or RNAs of a strain of *Campylobacter jejuni* to be carried out, the means for detecting the hybrids resulting from the preceding hybridization, when appropriate.

The invention also relates to a kit for sandwich hybridization assay, for the detection in vitro of *Campylobacter coli* strains in a biological sample, with said kit containing:

at least two probes targeting the same nucleic acid molecule and of which at least one is specific for *Campylobacter coli*, the buffer or components necessary for producing the buffer enabling hybridization reaction between these probes and the DNAs and/or RNAs of a strain of *Campylobacter coli* to be carried out, the means for detecting the hybrids resulting from the preceding hybridization, when appropriate.

The probes of the invention can be used also in a competition hybridization protocol.

In a competition hybridization, the target molecule competes with the hybrid formation between a specific probe and its complement. The more target is present, the lower the amount of hybrid formed between the probe and its complement. A positive signal, which indicates that the specific target was present, is seen by a decrease in hybridization reaction as compared with a system to which no target was added. In a particular embodiment, the specific oligonucleotide probe, conveniently labeled, is hybridized with the target molecule. Next, the mixture is transferred to a recipient (e.g. a microtiter dish well) in which a oligonucleotide complementary to the specific probe is fixed and the hybridization is continued. After washing, the hybrids between the complementary oligonucleotide and the probe are measured, preferably quantitatively, according to the label used.

The oligonucleotides of the invention can be used either as amplification primers in the polymerase chain reaction technique (PCR; Mullis and Faloona, Methods in Enzymology 155:335–350, 1987) to generate specific enzymatically amplified fragments and/or as probes to detect fragments amplified between bracketing oligonucleotide primers.

The specificity of a PCR-assisted hybridization assay can be controlled at different levels.

The amplification process or the detection process or both can be specific. The latter case, giving the highest specificity, is preferred. Such a highly specific PCR-assisted test can be developed using the probes of the invention.

However, in some occurrences, a non-specific amplification process, using conserved primers bracketing the detection probes of the invention, coupled to a specific detection, might be advantageous in order to standardize the amplification process in such way that it can be used for a great variety of organisms.

Amplification primers to be used in a standardized amplification process can be found in the conserved region of the 16S and 23S rRNA gene flanking the spacer region (see Example 1).

The invention also relates to a process for the in vitro detection of one microorganism or to the simultaneous in vitro detection of several microorganisms contained in a biological sample using any of the probes of the invention and specific for the microorganisms) to be detected, wherein the DNA and/or RNA present in the biological sample (and comprising the target sequence) is labeled, preferably using enzymatic amplification with at least one set of primers flanking the probe region, and wherein said biological sample is contacted with a membrane on which one or more oligonucleotide probes are dot spotted on a known location, in a medium enabling specific hybridization of the amplified target sequence and the probes on the membrane and wherein the hybrids resulting from the hybridizations are detected by appropriate means.

When amplification is necessary, its aim is to amplify the target sequence (whereby the amplification of the flanking regions of the target sequence also occurs) and to label only the amplified regions.

When there is enough target sequence in the biological sample, amplification is not needed.

In such a case, labeling has to be carried out, for instance, either chemically or by addition of specific dyes, prior to hybridization and it is to be noted that all the DNA and/or RNA present in the biological sample is labeled.

The invention also relates to a kit for the in vitro detection of one microorganism or for the simultaneous in vitro detection of several microorganisms contained in a biological sample, with said-kit containing:

at least one of the probes according to the invention and specific for the microorganism(s) to be detected, which is dot spotted to a membrane, the primers needed for performing enzymatic amplification of the DNA and/or RNA containing the target sequence of the above-mentioned probe, when appropriate, the buffers or components necessary for producing the buffers enabling enzymatic amplification and/or enabling a hybridization reaction between these probes and the DNAs and/or RNAs of a microorganism or microorganisms which are to be detected to to be carried out, the means for detecting the hybrids resulting from the preceding hybridization, when appropriate.

The above-mentioned process and kit involve the reversed hybridization dot-blot assay, such as the reversed dot-blot assay described by Saiki et al. (Proc. Natl. Acad. Sci. USA, 86:6230–6234, 1989).

In this case, the target sequences can first be enzymatically amplified using PCR with 5' biotinylated primers. In a second step, the amplified products are detected upon hybridization with specific oligonucleotides immobilized on a solid support. Several modifications of this technique can be envisaged such as the one described in Example 2. For example, this technique may be particularly advantageous for the simultaneous and specific detection of a variety of microorganisms which may be present in a particular clinical sample after PCR with universal primers flanking the spacer region and hybridization with a membrane on which different specific oligonucleotide probes for the organisms of interest are dot-spotted. Some examples of advantageous panels of specific oligonucleotide probes which can be used in a reversed hybridization assay as described above are:

(i) sputum-panel: *Moraxella (Branhamella) catarrhalis Streptococcus pneumoniae Haemophilus influenzae*
(ii) CSF-panel: *Neisseria meningitidis Haemophilus influenzae Streptococcus pneumoniae*
(iii) Urogenital-panel: *Neisseria gonorrhoeae Haemophilus ducreyi Chlamydia trachomatis Treponema pallidum*

Evidently these panels can be extended by adding probes for other clinically relevant micro-organisms. Also panels for other clinical samples, such as samples coming from peridontal pockets or blood samples, may be of interest.

For the PCR also nonuniversally conserved primers, for instance primers located in the spacer region itself, can be used and the PCR can be performed either with one set of primers or with different sets of primers in the same reaction vessel.

Reversed hybridization may also be carried out without an amplification step. In that particular case, the nucleic acids present in the sample have to be labeled or modified, specifically or not, for instance, chemically or by addition of specific dyes, prior to hybridization.

In most cases, the number of specific probes for the organisms of interest which can be derived from the spacer regions is not limited to the probes described in this text.

For some organisms only one or two probes are described to demonstrate the feasibility of spacer regions for the development of highly specific and sensitive probes for a variety of bacteria. The only exception is *Bordetella pertussis* for which only one particular region (from nucleotide 271 to 299 in the *Bordetella pertussis* sequence; FIG. 2, top line) of the spacer region has a specific sequence. However, from the spacer region sequence of *Bordetella pertussis*, probes may be devised which can be valuable in the simultaneous detection of highly related Bordetella species. Probes which detect Bordetella species other than *Bordetella pertussis* may also be deduced from the sequences disclosed in FIG. 2. Likewise, potentially specific probes for *Moraxella nonliguefaciens* and *Haemophilus influenzae* biogroup *aegyptius* may be inferred from the spacer region sequence shown in FIGS. 7 and 8, respectively.

The invention also relates to a kit for the in vitro detection of one ore more *Neisseria gonorrhoeae* strains in a biological sample, with said kit containing:

at least one probe selected among any of those according to the invention and specific for *Neisseria gonorrhoeae*, which is fixed to a solid support, the primers needed for performing enzymatical amplification of the DNA and/or RNA containing the target sequence of the above-mentioned probe, when appropriate, the buffers or components necessary for producing the buffers enabling enzymatical amplification and/or enabling hybridization reaction between said probe and the DNAs and/or RNAs of a strain of *Neisseria gonorrhoeae* to be carried out, the means for detecting the hybrids resulting from the preceding hybridization, when appropriate.

The invention also relates to a kit for the in vitro-detection of one ore more *Neisseria meningitidis* strains in a biological sample, with said kit containing:

at least one probe selected among any of those according to the invention and specific for *Neisseria meningitidis*, which is fixed to a solid support, the primers needed for performing enzymatical amplification of the DNA and/or RNA containing the target sequence of the above-mentioned probe, when appropriate, the buffers or components necessary for producing the buffers enabling enzymatical amplification and/or enabling hybridization reaction between said probe and the DNAs and/or RNAs of a strain of *Neisseria meningitidis* to be carried out, the means for detecting the hybrids resulting from the preceding hybridization, when appropriate.

The invention also relates to a kit for the in vitro detection of one ore more *Haemophilus ducreyi* strains in a biological sample, with said kit containing:

at least one probe selected among any of those according to the invention and specific for *Haemophilus ducreyi*, which is fixed to a solid support, the primers needed for performing enzymatical amplification of the DNA and/or RNA containing the target sequence of the above-mentioned probe, when appropriate, the buffers or components necessary for producing the buffers enabling enzymatical amplification and/or enabling hybridization reaction between said probe and the DNAs and/or RNAs of a strain of *Haemophilus ducreyi* to be carried out, the means for detecting the hybrids resulting from the preceding hybridization, when appropriate.

The invention also relates to a kit for the in vitro detection of one ore more *Branhamella catarrhalis* strains in a biological sample, with said kit containing:

at least one probe selected among any of those according to the invention and specific for *Branhamella catarrhalis*, which is fixed to a solid support, the primers needed for performing enzymatical amplification of the DNA and/or RNA containing the target sequence of the above-mentioned probe, when appropriate, the buffers or components necessary for producing the buffers enabling enzymatical amplification and/or enabling hybridization reaction between said probe and the DNAs and/or RNAs of a strain of *Branhamella catarrhalis* to be carried out, the means for detecting the hybrids resulting from the preceding hybridization, when appropriate.

The invention also relates to a kit for the in vitro detection of one ore more *Bordetella pertussis* strains in a biological sample, with said kit containing at least one probe selected among any of those according to the invention and specific for *Bordetella pertussis*, which is fixed to a solid support, the primers needed for performing enzymatical amplification of the DNA and/or RNA containing the target sequence of the above-mentioned probe, when appropriate, the buffers or components necessary for producing the buffers enabling enzymatical amplification and/or enabling hybridization reaction between said probe and the DNAs and/or RNAs of a strain of *Bordetella pertussis* to be carried out, the means for detecting the hybrids resulting from the preceding hybridization, when appropriate.

The invention also relates to a kit for the in vitro detection of one ore more *Haemophilus influenzae* strains in a biological sample, with said kit containing:

- at least one probe selected among any of those according to the invention and specific for *Haemophilus influenzae*, which is fixed to a solid support,
- the primers needed for performing enzymatical amplification of the DNA and/or RNA containing the target sequence of the above-mentioned probe, when appropriate,
- the buffers or components necessary for producing the buffers enabling enzymatical amplification and/or enabling hybridization reaction between said probe and the DNAs and/or RNAs of a strain of *Haemophilus influenzae* to be carried out,
- the means for detecting the hybrids resulting from the preceding hybridization, when appropriate.

The invention also relates to a kit for the in vitro detection of one ore more *Streptococcus pneumoniae* strains in a biological sample, with said kit containing:

- at least one probe selected among any of those according to the invention and specific for *Streptococcus pneumoniae*, which is fixed to a solid support,
- the primers needed for performing enzymatical amplification of the DNA and/or RNA containing the target sequence of the above-mentioned probe, when appropriate,
- the buffers or components necessary for producing the buffers enabling enzymatical amplification and/or enabling hybridization reaction between said probe and the DNAs and/or RNAs of a strain of *Streptococcus pneumoniae* to be carried out,
- the means for detecting the hybrids resulting from the preceding hybridization, when appropriate.

The invention also relates to a kit for the in vitro detection of one ore more *Streptococcus agalactiae* strains in a biological sample, with said kit containing:

- at least one probe selected among any of those according to the invention and specific for *Streptococcus agalactiae*, which is fixed to a solid support,
- the primers needed for performing enzymatical amplification of the DNA and/or RNA containing the target sequence of the above-mentioned probe, when appropriate,
- the buffers or components necessary for producing the buffers enabling enzymatical amplification and/or enabling hybridization reaction between said probe and the DNAs and/or RNAs of a strain of *Streptococcus agalactiae* to be carried out,
- the means for detecting the hybrids resulting from the preceding hybridization, when appropriate.

The invention also relates to a kit for the in vitro detection of one ore more *Campylobacter jejuni* and *Campylobacter coli* strains in a biological sample, with said kit containing:

- at least one probe selected among any of those according to the invention and specific for *Campylobacter jejuni*, and at least one probe selected among any of those according to the invention and specific for *Campylobacter coli*, which is fixed to a solid support,
- the primers needed for performing enzymatical amplification of the DNA and/or RNA containing the target sequence of the above-mentioned probes, when appropriate,
- the buffers or components necessary for producing the buffers enabling enzymatical amplification and/or enabling hybridization reaction between said probes and the DNAs and/or RNAs of a strain of *Campylobacter jejuni* and *Campylobacter coli* to be carried out,
- the means for detecting the hybrids resulting from the preceding hybridization, when appropriate.

CONDITIONS FOR THE USE OF PROBES

The probes of the invention are advantageously labeled. Any conventional label can be used. The probes can be labeled by means of radioactive tracers such as $^{32}P$, $^{35}S$, $^{125}I$, $^{3}H$ and $^{14}C$.

The radioactive labeling can be carried out according to any conventional method such as terminal labeling at the 3' or 5' position with the use of a radiolabeled nucleotide, a polynucleotide kinase (with or without dephosphorylation by a phosphatase), a terminal transferase, or a ligase (according to the extremity to be labeled). One of the probes of the invention can be the matrix for the synthesis of a chain consisting of several radioactive nucleotides or of several radioactive and nonradioactive nucleotides.

The probes of the invention can also be prepared by chemical synthesis using one or several radioactive nucleotides. Another method for radioactive labeling is a chemical iodination of the probes of the invention which leads to the binding of several $^{125}I$ atoms on the probes.

If one of the probes of the invention is made radioactive to be used for hybridization with a nonradioactive RNA or DNA, the method of detecting hybridization will depend on the radioactive tracer used. Generally, autoradiography, liquid scintillation, gamma counting or any other conventional method enabling one to detect an ionizing ray issued by the radioactive tracer can be used.

Nonradioactive labeling can also be used by associating the probes of the invention with residues having: immunological properties (e.g. antigen or hapten), a specific affinity for some reagents (e.g. ligand), properties providing a detectable enzymatic reaction (e.g. enzyme, co-enzyme, enzyme substrate or substrate taking part in an enzymatic reaction), or physical properties such as fluorescence, emission or absorption of light at any wavelength. Antibodies which specifically detect the hybrids formed by the probe and the target can also be used.

A nonradioactive label can be provided when chemically synthesizing a probe of the invention, the adenosine, guanosine, cytidine, thymidine and uracyl residues thereof being liable to be coupled to other chemical residues enabling the detection of the probe or the hybrids formed between the probe and a complementary DNA or RNA fragment.

However, the nucleotidic sequence of the probe, when modified by coupling one or more nucleotides to other chemical residues, would be the same as the nucleotide sequence of one of the probes of the invention.

The invention also relates to processes for detecting RNA and/or DNA with the probes of the invention by hybridization, which have been labeled and can be detected as described above. In this regard, conventional methods of hybridization can be used.

For detecting cells derived from or themselves being living organisms, the RNA and/or DNA of these cells, if need be, is made accessible by partial or total lysis of the cells using chemical or physical processes, and contacted with one or several probes of the invention which can be detected. This contact can be carried out on an appropriate support such as a nitrocellulose, cellulose, or nylon filter in a liquid medium or in solution. This contact can take place under suboptimal, optimal conditions, or under restrictive conditions (i.e. conditions enabling hybrid formation only if the sequences are perfectly homologous on a length of molecule). Such conditions include temperature, concentration of reactants, the presence of substances lowering the optimal temperature of pairing of nucleic acids (e.g. formamide, dimethylsulfoxide and urea) and the presence of substances apparently lowering the reaction volume and/or accelerating hybrid formation (e.g. dextran sulfate, polyethyleneglycol or phenol).

The elimination of a probe of the invention which has not hybridized can be carried out by washing with a buffer solution of appropriate ionic strength and at an appropriate temperature, with or without treatment with S1 nuclease or any other enzyme digesting single-strand DNA or RNA but not digesting DNA-RNA hybrids or double-strand DNA.

In a liquid medium, the hybrids of the probe of the invention paired to the cellular DNA or RNA fragments can be separated from the rest of the liquid medium in different ways, e.g. by chromatography over hydroxyapatite.

Then the hybridized probes are detected by means of the label on the probe.

In order to target the chromosomal DNA fragments, after treating RNA by one or several enzymes and denaturation of DNA fragments (i.e. separation of both chains), one of the probes of the invention is contacted with the DNA fragments under the conditions enabling hybridization, and after the time necessary to reach the end of the hybridization, the non-hybridized fragments are separated from the hybridized fragments and the label is detected as described above for the detection of the cells.

Generally speaking, the different probes of the invention can also be contained in recombinant DNA enabling their cloning, if the presence of a heterologous DNA is not a nuisance for the specificity of the probes in the encompassed uses.

In FIGS. 1 to 10, alignments of spacer regions (completely or partially sequenced) found in various microorganisms are shown as examples. matches and gaps are indicated by ":" and "-", respectively. For all sequences, the noncoding strand is shown in its 5'-3' orientation.

The 5' end is proximal to the 16S rRNA gene, the 3' end proximal to the 23S rRNA gene.

It is to be pointed out that each nucleic acid sequence of the spacer region between the 16S and 23S rRNA genes of each respective organism referred to in FIGS. 1 to 10 (except the one of *E. coli*) is new.

In FIG. 1 the nucleic acid sequence alignment of the 16S rRNA proximal end of the spacer region between the 16S and 23S rRNA gene of *Neisseria gonorrhoeae* strains NCTC 8375 (SEQ ID NO:85) (top line) and ITM 4367 (SEQ ID NO:86) (bottom line) is shown.

In FIG. 2 the nucleic acid sequence alignment of the spacer region between the 16S and 23S rRNA of *Bordetella pertussis* ATCC 10380 (SEQ ID NO:87) (top line) and *Bordetella bronchiseptica* NCTC 452 (SEQ ID NO:88) (bottom line) is shown.

In FIG. 3 the nucleic acid sequence alignment of the spacer region between the 16S and 23S rRNA of *Neisseria meningitidis* NCTC 10025 (SEQ ID NO:89) (top line) and *Neisseria gonorrhoeae* NCTC 8375 (SEQ ID NO:85) (bottom line) is shown.

In FIG. 4 the nucleic acid sequence alignment of the spacer region between the 16S and 23S rRNA of *Neisseria gonorrhoeae* NCTC 8375 (SEQ ID NO:85) (top line) and *Bordetella pertussis* ATCC 10380 (SEQ ID NO:87) (bottom line) is shown.

In FIG. 5 the nucleic acid sequence alignment of the spacer region between the 16S and 23S rRNA of Branhamella catarrhalis ITM 4197 (SEQ ID NO:90) (top line) and *Neisseria gonorrhoeae* NCTC 8375 (SEQ ID NO:85) (bottom line) is shown.

In FIG. 6 the nucleic acid sequence alignment of the spacer region between the 16S and 23S rRNA of *Haemophilus ducreyi* CIP 542 (SEQ ID NO:91) (top line) and *Escherichia coli* (bottom line) is shown.

In FIG. 7 the nucleic acid sequence alignment of the spacer region between the 16S and 23S rRNA of *Branhamella catarrhalis* LTM 4197 (SEQ ID NO:90) (top line) and *Moraxella nonliguefaciens* ATCC 19975 (SEQ ID NO:92) (bottom line) is shown.

In FIG. 8 the nucleic acid sequence alignment of the spacer region between the 16S and 23S rRNA of *Haemophilus influenzae* (biogroup *influenzae*) NCTC 8143 (SEQ ID NO:93) (top line) and *Haemophilus influenzae* (biogroup *aegyptius*) ITM 859 (SEQ ID NO:94) (bottom line) is shown.

In FIG. 9 the nucleic acid sequence alignment of the spacer region between the 16S and 23S rRNA of *Streptococcus pneumoniae* S90-5122 (SEQ ID NO:95) (top line) and Streptococcus agalactiae U90-2817 (SEQ ID NO:96) (bottom line) is shown.

In FIG. 10 the nucleic acid sequence alignment of the 23S rRNA proximal end of the spacer region between the 16S and 23S rRNA of *Campylobacter jejuni* ATCC 33560 (SEQ ID NO:97) (top line) and *Campylobacter coli* ATCC 33559 (SEQ ID NO:98) (bottom line) is shown.

The strains used can be obtained at the respective culture collections:

ATCC: American Type Culture Collection, Rockville, Md., USA.
CIP: Collection de l'Institut Pasteur, Paris, France.
ITM: Institute of Tropical Medicine, Antwerp, Belgium.
NCTC: National Collection of Type Cultures, Central Public Health Laboratory, London, United Kingdom.

The examples hereafter relate to the preparation of the probes of the invention and the experimental results with respect to the specificity and sensitivity of the probes using different hybridization protocols. The following organisms of clinical relevance were selected: *Neisseria gonorrhoeae, Neisseria meningitidis, Branhamella catarrhalis, Haemophilus ducreyi, Haemophilus influenzae*, and *Bordetella pertussis*.

The examples illustrate that species-specific and highly sensitive probes could readily be found in the spacer region of all organisms studied. Moreover, it is shown that probes could be constructed from this region for organisms for which no species-specific and highly sensitive probe could be found in the 16S and/or 23S rRNA molecule. The methods used are essentially the same as described by ROSSAU et al., J. Gen. Microbiol.; 135: 1735–1745, 1989; or in the European patent application n· 8940/045.3 unless otherwise stated. All methods used with the possible exception of enzymatical amplification of rRNA gene fragments and reversed hybridization, are currently known to people skilled in the art. The enzymatical amplification of rRNA gene fragments spanning the 16S–23S rRNA spacer region was obtained by the polymerase chain reaction technique (PCR) performed according to the recommendations given in the "Gene Amp" kit of Perkin Elmer Cetus. Nucleotides corresponding to conserved or semi-conserved regions in the rRNA molecules were used as PCR primers. The principle and protocol of the reversed dot-blot is described by Saiki et al. (1989).

EXAMPLE 1

*Neisseria meningitidis* and *Neisseria gonorrhoeae* both are important human pathogens, responsible for meningitidis and gonorrhoeae, respectively. These organisms are very closely related and their differentiation from one another and other Neisseria species is error-prone. DNA probes specific for *Neisseria meningitidis* and *Neisseria gonorrhoeae* may aid in the correct differentiation between both Neisseria species and may be used for direct detection of these species in clinical samples.

A number of DNA probes have been described for the detection of *Neisseria gonorrhoeae* (European Patent Application nr 0272 009 and 0337 896; URDEA et al., Clin. Chem. 35: 1571–1575, 1989; TOTTEN et al., J. Infect. Dis. 148: 462–471, 1989; DONEGAN et al., Mol. Cell. Probes 3: 13–26, 1989; KOLBERG et al., Mol. Cell. Probes 3: 59–72, 1989). However, some of these probes were found to cross-react with non-*Neisseria gaonorrhoeae* strains or were not highly sensitive. None of these probes were derived from the 16S–23S rRNA spacer region.

A DNA probe which detects *Neisseria meningitidis* strains has also been described (KOLBERG et al., Mol. Cell. Probes 3: 59–72, 1989). This probe, devised from the pilin gene of *Neisseria gonorrhoeae*, was neither highly specific nor highly sensitive for *Neisseria meningitidis*.

The sequence of the spacer region between the 16S and 23S rRNA gene of the type strains of *Neisseria gonorrhoeae* and *Neisseria meningitidis* was determined using cloned material originating from a PCR fragment spanning the spacer region. The alignment of both sequences, shown in FIG. 3, revealed several potential probe sequences.

An unexpected inserted sequence of about 60 base pairs were detected in the spacer region of the *Neisseria meningitidis* strain. Oligonucleotides with the following sequences were derived from this inserted sequence:

GGTCAAGTGT GACGTCGCCC TG (SEQ ID NO:9) NMI1

GTTCTTGGTC AAGTGTGACG TC (SEQ ID NO:13) NMI2

Also in another area of the spacer region (from base pairs 365 to 386 in the *Neisseria meningitidis* sequence in FIG. 3) a substantial degree of mismatch was revealed between *Neisseria meningitidis* and *Neisseria gonorrhoeae*. From this area, two oligonucleotide probes (NMI3 and NGI1 for the detection of *Neisseria meningitidis* and *Neisseria gonorrhoeae*, respectively) were chemically synthesized:

GCGTTCGTTA TAGCTATCTA CTGTGC (SEQ ID NO:17) NMI3

CGATGCGTCG TTATTCTACT TCGC (SEQ ID NO:1) NGI1

These nucleotides were $^{32}$P-labeled at their 5' ends using polynucleotide kinase or tailed at their 3' ends with digoxigenated UTP using terminal transferase and used as hybridization probes. As target, dot-spotted denatured genomic DNA from a large number of *Neisseria meningitidis* and *Neisseria gonorrhoeae* strains obtained from different locations and several strains from other bacterial taxa was used.

The hybridization-mixture was either 3×SSC, 25 mM potassium phosphate buffer, pH 7, deionized formamide (20%, v/v), Ficoll (0.02%, w/v), bovine serum albumin (0.02%, w/v), polyvinylpyrrolidone (0.02%, w/v) and sheared, denatured salmon sperm DNA (0.1 mg/ml) or the solution given in the protocol sheet of the nonradioactive DNA labeling and detection kit (Boehringer Mannheim) except that 3×SSC (1×SSC is: 0.15 M NaCl, 0.015 M sodium citrate, pH 7.0) instead of 5×SSC was used and formamide was added up to 20% (v/v). The wash solution contained 3×SSC, 20% formamide and 25 mM phosphate buffer pH 7.1.

The hybridization results are summarized in the table below. The hybridization and wash temperature for each probe is indicated between parenthesis. All probes tested proved to be highly specific and highly sensitive for *Neisseria gonorrhoeae* (probe NGI1) or *Neisseria meningitidis* (probes NMI1, NMI2 and NMI3).

|  | No. positive strains/No. strains tested | | | |
|---|---|---|---|---|
| TAXON | NMI1 (45° C.) | NMI2 (45° C.) | NMI3 (40° C.) | NGI1 (50° C.) |
| *Neisseria meningitidis* | 52/53 | 10/11 | 56/56 | 0/11 |
| Neisseria sp ATCC 43831 | 1/1 | 1/1 | 1/1 | 0/1 |
| *Neisseria gonorrhoeae* | 0/16 | 0/9 | 0/10 | 10/10 |
| *Neisseria polysaccharea* | 0/3 | — | 0/3 | 0/3 |
| *Neisseria lactamica* | 0/10 | — | 0/10 | 0/10 |
| *Neisseria cinerea* | 0/4 | — | 0/4 | 2/4 |
| *Neisseria mucosa* | 0/3 | — | 0/3 | 0/3 |
| *Neisseria macacae* | 0/1 | — | 0/1 | 0/1 |
| *Neisseria flavescens* | 0/1 | — | 0/1 | 0/1 |
| *Neisseria subflava* | 0/2 | — | 0/2 | 0/2 |
| *Neisseria sicca* | 0/1 | — | 0/1 | 0/1 |
| *Neisseria elongata* | 0/2 | — | 0/2 | 0/2 |
| *Neisseria canis* | 0/1 | — | 0/1 | 0/1 |
| *Neisseria animalis* | 0/1 | — | 0/1 | 0/1 |
| *Neisseria denitrificans* | 0/1 | — | 0/1 | 0/1 |
| Neisseria sp | 0/5 | — | 0/4 | 0/3 |
| CDC group M-5 | 0/1 | — | 0/1 | 0/1 |
| CDC group EF-4a | 0/1 | — | 0/1 | 0/1 |
| *Kingella denitrificans* | 0/2 | — | 0/1 | 0/1 |
| *Kingella kingae* | 0/1 | — | 0/1 | 0/1 |
| *Simonsiella muelleri* | 0/1 | — | 0/1 | 0/1 |
| *Simonsiella crassa* | 0/1 | — | 0/1 | 0/1 |
| *Simonsiella steedae* | 0/1 | — | 0/1 | 0/1 |
| Simonsiella sp | 0/1 | — | 0/1 | 0/1 |
| *Alysiella filiformis* | 0/1 | — | 0/1 | 0/1 |
| *Eikenella corrodens* | 0/2 | — | 0/2 | 0/2 |
| *Chromobacterium violaceum* | 0/1 | — | 0/1 | 0/1 |
| *Iodobacter fluviatile* | 0/1 | — | 0/1 | 0/1 |
| *Aquaspirilum dispar* | 0/1 | — | 0/1 | 0/1 |
| *Comamonas testosteroni* | 0/1 | — | 0/1 | 0/1 |
| *Haemophilus influenzae* | 0/1 | — | — | — |
| *Haemophilus ducrevi* | 0/1 | — | 0/1 | 0/1 |
| *Kingella indologenes* | 0/1 | — | 0/1 | 0/1 |
| *Moraxella lacunata* | 0/1 | — | — | — |
| *Moraxella nonliquefaciens* | 0/1 | — | — | — |
| *Moraxella catarrhalis* | 0/3 | — | 0/2 | 0/2 |
| *Moraxella cuniculi* | 0/1 | — | — | — |
| *Moraxella caviae* | 0/1 | — | — | — |
| *Moraxella ovis* | 0/1 | — | — | — |
| *Moraxella osloensis* | 0/1 | — | — | — |
| *Escherichia coli* | 0/1 | 0/1 | 0/1 | 0/1 |

The specificity of the detection with probes NMI3 and NGI3 was also checked after enzymatic amplification of the spacer regions with the following amplification primers:

TGGGTGAAGTCGTAACAAGGTA (SEQ ID NO:103) AP16

CAC GTC CTTCGTCGCCT (SEQ ID NO:104) AP23 located at the 3' end of the 16S rRNA gene and the 5' end of the 23S rRNA gene, respectively. One hundred nanograms of genomic DNA from a strain of *Neisseria gonorrhoeae*, *Neisseria meningitidis*, *Haemophilus ducreyi*, *Bordetella pertussis* and *Branhamella catarrhalis* was used in the PCR reaction. After amplification, 1/10 of the yield was loaded on an agarose gel, electrophoresed and blotted on a nylon membrane.

The membrane was consecutively hybridized with the probes NGI1 and NMI3.

Significant hybridization signals could only be detected in lanes where *Neisseria gonorrhoeae* or *Neisseria meningitidis* material was present when NGI1 or NMI3 was used as probe, respectively.

EXAMPLE 2

*Bordetella pertussis* is the causative agent of whooping cough. As a result of repeated vaccination-campaigns, the disease has become a minor problem in the industrialized countries. However, in third-world countries, *Bordetella pertussis* remains a leading cause of childhood mortality.

Strains of three Bordetella species (*Bordetella pertussis, Bordetella parapertussis* and *Bordetella bronchiseptica*) are extremely highly related (KLOOS et al., Int. J. Syst. Bacteriol. 31:173–176, 1981; DE LEY et al., Int. J. Syst. Bacteriol. 36:405–414, 1986) and should be considered as belonging to one genospecies. This genotypical relationship is also reflected in many other characteristics of these bacteria, thereby making their phenotypical differentiation tedious.

Clinical signs of pertussis often are atypical and laboratory diagnosis is needed. As yet, no sensitive, specific and rapid test exists. Culture still remains the method of choice, but recovery rates are low and the results usually are available only 3 to 7 days after inoculation (FRIEDMAN, Clin. Microbiol. Rev. 4:365–376, 1988; HALPERZIN et al., J. Clin. Microbiol. 27:752–757, 1989). A DNA probe-based assay may greatly improve the diagnosis of *Bordetella pertussis* infections.

Probes for the detection of *Bordetella pertussis* are described in the literature (PARK et al., FEMS Microbiol. Lett. 52:19–24, 1988; McPHEAT and McNALLY, J. Gen. Microbiol. 133:323–330, 1987 and FEMS Microbiol. Lett. 41:357–360, 1987; McLAFFERTY et al., Abstracts of the Annual Meeting of the American Society for Microbiology C-168, 1986, and C-322, 1987). The probe described by McLAFFERTY et al. (1986 and 1987) is not highly specific. For the other probes described, the data presented are to scanty to infer the degree of specificity and sensitivity.

Part of the ribosomal RNA gene of the following strains were enzymatically amplified and cloned in a plasmid vector: *Bordetella pertussis* ATCC 10380, *Bordetella parapertussis* NCTC 5952 (type strain), and *Bordetella bronchiseptica* NCTC 452 (type strain). The cloned fragments of the different species were partially sequenced using the dideoxy chain termination method and their sequences were compared. The sequence information concerning the 16S rRNA gene which became available, indicated that no species-specific probes could be devised (ROSSAU et al., unpublished). However, as shown in the alignment in FIG. 2, a non-homologous area (from basepairs 271 to about 300) was found in the spacer region between the 16S and 23S rRNA genes of the *Bordetella pertussis* and the *Bordetella bronchiseptica* strain.

The sequence of the spacer region of the *Bordetella parapertussis* strain was virtually identical to the *Bordetella bronchiseptica* sequence (ROSSAU et al., unpublished).

From the area between nucleotide 271 and 295 in the spacer region of *Bordetella pertussis* a oligonucleotide probe with the following sequence was derived:
CCACACCCAT CCTCTGGACA GGCTT (SEQ ID NO: 53) BPI1

The oligonucleotide probe was chemically synthesized and labeled with digoxigenin-UTP using terminal transferase. The results obtained with dot-spotted denatured genomic DNA as target are summarized in the table below.

| TAXON | Hybridization with BPI1 at 55° C. No. positive strains/No. strains tested |
|---|---|
| *Bordetella pertussis* | 4/4 |
| *Bordetella parapertussis* | 0/3 |
| *Bordetella bronchiseptica* | 0/3 |
| *Alcaligenes denitrificans* | 0/1 |
| *Alcaligenes paradoxus* | 0/1 |
| *Oligella ureolytica* | 0/1 |
| *Oligella urethralis* | 0/1 |
| *Taviorella equiqenitalis* | 0/1 |
| *Pseudomonas cepacia* | 0/1 |
| *Pseudomonas solanacearum* | 0/1 |
| *Couamonas testosteroni* | 0/1 |
| *Neisseria meningitidis* | 0/1 |
| *Branhamella catarrhalis* | 0/1 |
| *Haemophilus influenzae* | 0/1 |

Under the conditions used, the probe BPI1 proved to be 100% specific and 100% sensitive for *Bordetella pertussis*.

The hybridization mixture was as described in the protocol sheet of the nonradioactive DNA labeling and detection kit (Boehringer Mannheim) except that 3×SSC (1×SSC is: 0.15 M NaCl, 0.015 M sodium citrate, pH 7.0) instead of 5×SSC was used and formamide was added up to 20% (v/v). The wash solution contained 3× SSC, 20% formamide and 25 mM phosphate buffer pH 7.1. The hybridization and wash temperature was 55° C.

Essentially the same result as those shown in the table above were obtained when using a reversed dot-blot assay. This assay was performed as follows:

One ng of bacterial DNA from a variety of strains obtained from different bacterial species was enzymatically amplified as recommended by the manufacturer of the Gene-Amp kit (Perkin Elmer Cetus) except that digoxigenin-11-dUTP (Boehringer Mannheim) was added to the amplification mixture to a final concentration of 40 µM. Thirty cycles (1 min/95° C., 1 min/50° C., 1 min/72° C.) with the primers AP16 and AP23 (see example 1) were performed in a total of 50 µl, whereafter 5 µl of each PCR mix was added to 1 ml of hybridization mixture (composition as defined above) in the presence of a membrane to which 0.2 pmol, 0.02 pmol and 0.002 pmol of probe BPI1 was fixed. The hybridization proceeded for one hour at 55° C. The wash step was performed at the same temperature for 10 min. The detection was performed as described in the non-radioactive DNA labeling and detection kit (Boehringer Mannheim). Although a distinct band could be observed in all samples examined after gel electrophoresis and ethidium bromide staining using the reversed dot-blot protocol, a clearly positive signal was obtained exclusively with samples in which *Bordetella pertussis* DNA was present.

EXAMPLE 3

*Branhamella catarrhalis*, also known as *Moraxella catarrhalis* or *Neisseria catarrhalis*, is a fastidious, biochemically rather inert bacterium. Recently its important pathogenic potential was recognized.

*Branhamella catarrhalis* seems to be frequently involved in serious infections of the respiratory tract (HAGER et al., Rev. Infect. Dis. 9:1140–1149, 1987). The diagnosis of *Branhamella catarrhalis* requires culture of the organism, which may be hampered due to overgrowth by less fastidious micro-organisms, and a battery of phenotypical tests to distinguish this organisms from commensals, such as Neisseria species, present in the oral cavity.

In some occurrences the phenotypical test are inconclusive as to the identity of the presumptive *Branhamella catarrhalis* isolate since there only are a limited number of tests which differentiate *Branhamella catarrhalis* from phenotypical similar bacteria (RIOU and GUIBOURDENCHE, Drugs 31 [suppl.3]:1–6, 1986). The use of a DNA probe based assay may considerably simplify the laboratory diagnosis of *Branhamella catarrhalis*. A DNA probe for *Branhamella catarrhalis* derived from an unspecified DNA fragment and which cross-hybridized with DNA from *Neisseria caviae* was described by BEAULIEU and ROY (Abstracts of the Annual Meeting of the American Society for Microbiology, Abstract No. D-249, 1989).

Part of the rRNA gene of Branhamella catarrhalis ITG 4197 was enzymatieally amplified by the polymerase chain reaction technique and cloned in a plasmid vector. The fragment spanning the 16S–23S rRNA spacer region was subsequently sequenced by the dideoxy chain termination technique. THe sequence is shown in FIG. 7 (top line). From the sequence data, the following oligonucleotide was selected and chemically synthesized:
TTAAACATCT TACCAAAG (SEQ ID NO:33) BCI1

The oligonucleotide was $^{32}$P-labeled at its 5' end with polynucleotide kinase and used as a hybridization probe. As target, dot-spotted denatured genomic DNA of 31 *Branhamella catarrhalis* strains from different locations and 19 strains of other bacterial taxa was used.

The hybridization-mixture was either 3×SSC (1×SSC is: 0.15 M NaCl, 0.015 M sodium citrate, pH 7.0), 25 mM potassium phosphate buffer, pH 7, deionized formamide (20%, v/v), Ficoll (0.02%, w/v), bovine serum albumin (0.02%, w/v), polyvinylpyrrolidone (0.02%, w/v) and sheared, denatured salmon sperm DNA (0.1 mg ml-1). The wash-solution contained 3×SSC, 20% formamide and 25 mM phosphate buffer pH 7.1. The hybridization and wash temperature was 30° C.

Under the conditions used, probe BCI1 hybridized to all *Branhamella catarrhalis* strains. None of the strains tested belonging to other bacterial species gave a significant hybridization signal with the probe.

The non-*Branhamella catarrhalis* strains tested are:

| | |
|---|---|
| *Moraxella lacunata* | ATCC 17967 |
| *Moraxella lacunata* | ATCC 17952 |
| *Moraxella bovis* | ITM 1601 |
| *Moraxella nonliquefaciens* | ATCC 19975 |
| *Neisseria cuniculi* | ITM 3388 |
| *Neisseria ovis* | NCTC 11227 |
| *Neisseria caviae* | ATCC 14659 |
| *Alysiella sp.* | ATCC 29468 |
| *Moraxella osloensis* | LMG 1043 |
| *Moraxella osloensis* | ATCC 17974 |
| "*Moraxella paraphenylpyruvica*" | LMG 5125 |
| "*Moraxella camembertii*" | LMG 7022 |
| *Psychrobacter immobilis* | LMG 6784 |
| *Acinetobacter calcoaceticus* | ATCC 23055 |
| *Escherichia coli* | B |
| *Haemophilus influenzae* | NCTC 8143 |
| *Eikenella corrodens* | NCTC 10596 |
| *Xanthouonas maltophilia* | LMG 958 |
| *Xanthomonas campestris* | LMG 568 |

EXAMPLE 4

*Haemophilus ducreyi*, the causative agent of chancroid, is a fastidious Gram-negative bacterium. The culture of this organism is both difficult and insensitive; yet it still is the method of choice for the diagnosis of *Haemophilus ducreyi* infections. The use of highly specific probes may obviate the culture and increase the sensitivity of the diagnosis. Cloned DNA probes for *Haemophilus ducreyi* showing weak cross-reactivity with other Haemophilus and Pasteurella species, and targeting genes coding for proteins were described by PARSONS et al. (J. Clin. Microbiol. 27:1441–1445, 1989).

Part of the rRNA gene of the type strain of *Haemophilus ducreyi* CIP 542 was enzymatically amplified by the polymerase chain reaction and cloned in a plasmid vector.

The sequence of the spacer region between the 16S and 23S rRNA gene was obtained by the dideoxy chain termination technique. From the nucleic acid sequence, the following oligonucleotide was selected and chemically synthesized:
TTATTATGCG CGAGGCATAT TG (SEQ ID NO:41) HDI1

The oligonucleotide was $^{32}$P-labeled at its 5' ends or tailed at its 3' ends with digoxigenated UTP using terminal transferase and used as a hybridization probe.

As target, dot-spotted denatured genomic DNA of 41 *Haemophilus ducreyi* strains from different locations and several strains of other bacterial taxa was used. The oligonucleotide probe hybridized exclusively to all *Haemophilus ducreyi* strains tested.

The hybridization-mixture was either 3×SSC, 25 mM potassium phosphate buffer, pH 7, deionized formamide (20%, v/v), Ficoll (0.02%, w/v), bovine serum albumin (0.02%, w/v), polyvinylpyrrolidone (0.02%, w/v) and sheared, denatured salmon sperm DNA (0.1 mg ml-1) or the solution given in the protocol sheet of the nonradioactive DNA labeling and detection kit (Boehringer Mannheim) except that 3×SSC (1×SSC is: 0.15 M NaCl, 0.015 M sodium citrate, pH 7.0) instead of 5×SSC was used and formamide was added up to 20% (v/v). The wash solution contained 3×SSC, 20% formamide and 25 mM phosphate buffer pH 7.1. The hybridization and wash temperature was 40° C.

The non-*Haemophilus ducreyi* strains tested were:
*Escherichia coli* MC 1061
*Escherichia coli* B
*Actinobacillus actinomycetemcomitans* NCTC 9710
*Actinobacillus lignieresii* NCTC 4189
*Haemophilus aphrophilus* NCTC 5906
*Haemophilus influenzae* NCTC 8143
*Histophilus ovis* HIM 896–7
*Pasteurella multocida* NCTC 10322
*Branhamella catarrhalis* ITM 4197
*Comamonas testosteroni* ATCC 17407
*Oligella urethralis* IMG 6227
*Neisseria gonorrhoeae* ITM 4437
*Campylobacter jejuni* CCUG 11284
*Acinetobacter calcoaceticus* ATCC 23055
Unidentified strain ITM 3565

EXAMPLE 5

The Gram-negative bacterial species *Haemophilus influenzae* can be subdivided within two biogroups: *influenzae* and *aegyptius* (Casin et al., Ann. Inst. Pasteur/Microbiol. 137B:155–163, 1986). Organisms of the *influenzae* biogroup are important respiratory tract pathogens and also the cause of meningitis and otitis in children. Biogroup *aegyptius* isolates are the causative agent of bacterial conjunctivitis in hot climates and seem to be associated with Brazilian Purpuric Fever (Brenner et al., J. Clin. Microbiol. 26:1524–1534, 1988). A rapid detection of typable and non-typable *Haemophilus influenzae* strains can be achieved with nucleic acid probes.

DNA probes for this species have been described in the literature (Terpstra et al., Scand. J. Infect. Dis. 19:641–646, 1987: Malouin et al. J. Clin. Microbiol. 26:2132–2138, 1988). None of these probes have been derived from the 16S–23S rRNA spacer region.

Part of the rRNA gene of the type strain of *Haemophilus influenza*. NCTC 8143 was enzymatically amplified by the polymerase chain reaction and cloned in a plasmid vector.

The sequence of the spacer region between the 16S and 23S rRNA gene was obtained by the dideoxy chain termination technique. From the nucleic acid sequence, the following oligonucleotides were selected and chemically synthesized:

ACGCATCAAA TTGACCGCAC TT (SEQ ID NO:45) HII1
ACTTTGAAGT GAAAACTTAA AG (SEQ ID NO:49) HII2

The oligonucleotides were $^{32}$P-labeled at their 5' ends and used as hybridization probes. As target, dot-spotted denatured genomical DNA of bacterial taxa was used.

The hybridization results with both probes are summarized in the table below. At the hybridization and wash temperatures used, probe HII1 did not hybridize to the *Haemophilus influenzae* biogroup *aegyptius* strain. Probe HII2 hybridized to strains of both biogroups. Both probes also hybridized at the indicated temperatures to 15 other clinical isolates of *Haemophilus influenzae* biogroup *influenzae* obtained from the Institute of Tropical Medicine, Antwerp, Belgium.

The hybridization mixture was 3×SSC, 25 mM potassium phosphate buffer, pH 7, deionized formamide (20%, v/v), Ficoll (0.02%, w/v), bovine serum albumin (0.02%, w/v), polyvinylpyrrolidone (0.02%, w/v) and sheared, denatured salmon sperm DNA (0.1 mg ml-l). The wash solution contained 3×SSC, 20% formamide and 25 mM phosphate buffer pH 7.1.

| | PROBE. | |
|---|---|---|
| TAXON | HII1 (50° C.) | HII2 (30° C.) |
| *Haemophilus influenzae* (biogroup influenzae) NCTC 8143 | + | + |
| *Haemophilus influenzae* (biogroup influenzae) ITM 3837 | + | + |
| *Haemophilus influenzae* (biogroup aegypitus) ITM 859 | – | + |
| *Haemophilus parahaemolyticus* ITM 402 | – | – |
| *Haemophilus parainfluenzae* ITM 1094 | – | – |
| *Haemophilus aphrophilus* NCTC 5906 | – | – |
| *Haemophilus ducrevi* CIP 542 | – | – |
| *Pasteurella multocida* NCTC 10322 | – | – |
| *Pasteurella picida* ATCC 17911 | – | – |
| *Actinobacillus lignieresii* NCTC 4189 | – | – |
| *Actinobacillus actinomycetemcominitans* NCTC 9710 | – | – |
| *Histophilus ovis* HIM 896-7 | – | – |
| *Pseudomonas cepacia* ATCC 25609 | – | – |
| *Acinetobacter calcoaceticus* ATCC 23055 | – | – |
| *Branhamella catarrhalis* LMG 5128 | – | – |
| *Bordetella pertussis* NCTC 8189 | – | – |
| *Escherichia coil* B | – | – |
| *Neisseria meninqitidis* NCTC 10025 | – | – |

What is claimed is:

1. A method for in vitro detection of a microorganism contained in a biological sample comprising the steps of:

(a) contacting said biological sample with a nucleic acid probe, the contacting being at a sufficient temperature and hybridization solution concentration to form a hybrid with the nucleic acid probe, the nucleic acid probe consisting of:
   a sequence from a transcribed spacer region between the 16S and 23S rRNA genes of a prokaryotic microorganism and comprising about 15 to about 100 contiguous nucleotides from a transcribed spacer region between 16S and 23S rRNA genes of a prokaryotic microorganism, or a variant of the nucleic acid comprising up to 3 mismatches in a 15 residue nucleic acid and up to 7 mismatches in a 100 or more residue nucleic acid, wherein the probe specifically detects species of the prokaryotic microorganism and wherein said probe does not include sequences of a tRNA gene: and (b) detecting the formation of the hybrid, with the presence of the hybrid indicating the presence of the microorganism.

2. The method of claim 1, further comprising the step of making nucleic acids of the microorganism accessible to hybridization.

3. The method of claim 1, wherein the nucleic acids are made accessible to hybridization by amplification using at least two primers, wherein a first primer is complementary to a 5' flanking region of a spacer region between the 16S and 23S rRNA genes of prokaryotic microorganism; and a second primer is complementary to a 3' flanking region of the spacer region of the prokaryotic microorganism.

4. The method of claim 3, wherein the at least two primers hybridize to a conserved region of the 3'-end and the 5'-end of the 16S and 23S genes respectively, of the prokaryotic microorganisms to be detected.

5. The method of claim 3, wherein the at least two primers have the following sequences:

TGGCTCAGATTGAACGCTGGCGGC (SEQ ID NO:99) and

CCTTTCCCTCACGGTACTGGT (SEQ ID NO:100), or

TGGGTGAAGTCGTAACAAGGTA (SEQ ID NO:101) and

CACGTCCTTCGTCGCCT (SEQ ID NO:102).

6. The method of claim 1, wherein the sequence of the probe comprises a sequence of:

```
CGATGCGTCG TTATTCTACT TCGC (SEQ ID NO:1)                                       NGI1;
GCGAAGTAGA ATAACGACGC ATCG (SEQ ID NO:2)                                       NGI1IC;
GCGAAGUAGA AUAACGACGC AUCG (SEQ ID NO:3)                                       NGI1ICR;
CGAUGCGUCG UUAUUCUACU UCGC (SEQ ID NO:4)                                       NGI1R;
TTCGTTTACC TACCCGTTGA CTAAGTAAGC AAAC (SEQ ID NO:5)                            NGI2;
GTTTGCTTAC TTAGTCAACG GGTAGGTAAA CGAA (SEQ ID NO:6)                            NGI2IC;
GUUUGCUUAC UUAGUCAACG GGUAGGUAAA CGAA (SEQ ID NO:7)                            NGI2ICR;
UUGGUUUACC UACCCGUUGA CUAAGUAAGC AAAC (SEQ ID NO:8)                            NGI2R;
GGTCAAGTGT GACGTCGCCC TG (SEQ ID NO:9)                                         NMI1;
CAGGGCGACG TCACACTTGA CC (SEQ ID NO:10)                                        NMI1IC;
CAGGGCGACG UCACACUUGA CC (SEQ ID NO:11)                                        NMI1ICR;
GGUCAAGUGU GACGUCGCCC UG (SEQ ID NO:12)                                        NMI1R;
GTTCTTGGTC AAGTGTGACG TC (SEQ ID NO:13)                                        NMI2;
GACGTCACAC TTGACCAAGA AC (SEQ ID NO:14)                                        NMI2IC;
GACGUCACAC UUGACCAAGA AC (SEQ ID NO:15)                                        NMI2ICR;
GUUCUUGGUC AAGUGUGACG UC (SEQ ID NO:16)                                        NMI2R;
GCGTTCGTTA TAGCTATCTA CTGTGC (SEQ ID NO:17)                                    NMI3;
GCACAGTAGA TAGCTATAAC GAACGC (SEQ ID NO:18)                                    NNI3IC;
GCACAGUAGA UAGCUAUAAC GAACGC (SEQ ID NO:19)                                    NMI3ICR;
GCGUUCGUUA UAGCUAUCUA CUGUGC (SEQ ID NO:20)                                    NMI3R;
TGCGTTCGAT ATTGCTATCT ACTGTGCA (SEQ ID NO:21)                                  NMI4;
TGCACAGTAG ATAGCAATAT CGAACGCA (SEQ ID NO:22)                                  NMI4IC;
UGCACAGUAG AUAGCAAUAU CGAACGCA (SEQ ID NO:23)                                  NMI4ICR;
UGCGUUCGAU AUUGCUAUCU ACUGUGCA (SEQ ID NO:24)                                  NMI4R;
TTTTGTTCTTGGTCAAGTGTGACGTCGCCCTGAATGGATTCTGTTCCATT (SEQ ID NO:25)              NMI5;
AATGGAACAGAATCCATTCAGGGCGACGTCACACTTGACCAAGAACAAAA (SEQ ID NO:26)              NMI5C;
AAUGGAACAGAAUCCAUUCAGGGCGACGUCACACUUGACCAAGAACAAAA (SEQ ID NO:27)              NMI5ICR;
UUUUGUUCUUGGUCAAGUGUGACGUCGCCCUGAAUGGAUUCUGUUCCAUU (SEQ ID NO:28)              NMI5R;
TTTGCCTAAC ATTCCGTTGA CTAGAACATC AGAC (SEQ ID NO:29)                           NMI6;
GTCTGATGTT CTAGTCAACG GAATGTTAGG CAAA (SEQ ID NO:30)                           NMI6IC;
GUCUGAUGUU CUAGUCAACG GAAUGUUAGG CAAA (SEQ ID NO:31)                           NMI6ICR;
UUUGCCUAAC AUUCCGUUGA CUAGAACAUC AGAC (SEQ ID NO:32)                           NMI6R;
TTATTATGCG CGAGGCATAT TG (SEQ ID NO:41)                                        HDI1;
CAATATGCCT CGCGCATAAT AA (SEQ ID NO:42)                                        HDI1IC;
CAAUAUGCCU CGCGCAUAAU AA (SEQ ID NO:43)                                        HDI1ICR;
UUAUUAUGCG CGAGGCAUAU UG (SEQ ID NO:44)                                        HDI1R;
TTAAACATCT TACCAAAG (SEQ ID NO:33)                                             BCI1;
CTTTGGTAAG ATGTTTAA (SEQ ID NO:34)                                             BCI1IC;
CUUUGGUAAG AUGUUUAA (SEQ ID NO:35)                                             BCI1ICR;
UUAAACAUCU UACCAAAG (SEQ ID NO:36)                                             BCI1R;
```

-continued

| | |
|---|---|
| TTGATGTTTA AACTTGCTTG GTGGA (SEQ ID NO:37) | BCI2; |
| TCCACCAAGC AAGTTTAAAC ATCAA (SEQ ID NO:38) | BCI2IC; |
| UCCACCAAGC AAGUUUAAAC AUCAA (SEQ ID NO:39) | BCI2ICR; |
| UUGAUGUUUA AACUUGCUUG GUGGA (SEQ ID NO:40) | BCI2R; |
| CCACACCCAT CCTCTGGACA GGCTT (SEQ ID NO:53) | BPI1; |
| AAGCCTGTCC AGAGGATGGG TGTGG (SEQ ID NO:54) | BPI1IC; |
| AAGCCUGUCC AGAGGAUGGG UGUGG (SEQ ID NO:55) | BPI1ICR; |
| CCACACCCAU CCUCUGGACA GGCUU (SEQ ID NO:56) | BPI1R; |
| ACGCATCAAA TTGACCGCAC TT (SEQ ID NO:45) | HII1; |
| AAGTGCGGTC AATTTGATGC GT (SEQ ID NO:46) | HII1IC; |
| AAGUGGGGUC AAUUUGAUGC GU (SEQ ID NO:47) | HII1ICR; |
| ACGCAUCAAA UUGACCGCAC UU (SEQ ID NO:48) | HII1R; |
| ACTTTGAAGT GAAAACTTAA AG (SEQ ID NO:49) | HII2; |
| CTTTAAGTTT TCACTTCAAA GT (SEQ ID NO:50) | HII2IC; |
| CUUUAAGUUU UCACUUCAAA GU (SEQ ID NO:51) | HII2ICR; |
| ACUUUGAAGU GAAAACUUAA AG (SEQ ID NO:52) | HII2R; |
| AATCGAAAGG TTCAAATTGT T (SEQ ID NO:69) | SAI1; |
| AACAATTTGA ACCTTTCGAT T (SEQ ID NO:70) | SAI1IC; |
| AACAAUUUGA ACCUUUCGAU U (SEQ ID NO:71) | SAI1ICR; |
| AAUCGAAAGG UUCAAAUUGU U (SEQ ID NO:72) | SAI1R; |
| GGAAACCTGC CATTTGCGTC TT (SEQ ID NO:73) | SAI2; |
| AAGACGCAAA TGGCAGGTTT CC (SEQ ID NO:74) | SAI2IC; |
| AAGACGCAAA UGGCAGGUUU CC (SEQ ID NO:75) | SAI2ICR; |
| GGAAACCUGC CAUUUGCGUC UU (SEQ ID NO:76) | SAI2R; |
| TCCACGATCT AGAAATAGAT TGTAGAA (SEQ ID NO:77) | SAI3; |
| TTCTACAATC TATTTCTAGA TCGTGGA (SEQ ID NO:78) | SAI3IC; |
| UUCUACAAUC UAUUUCUAGA UCGUGGA (SEQ ID NO:79) | SAI3ICR; |
| UCCACGAUCU AGAAAUAGAU UGUAGAA (SEQ ID NO:80) | SAI3R; |
| TCTAGTTTTA AAGAAACTAG GTT (SEQ ID NO:81) | SAI4; |
| AACCTAGTTT CTTTAAAACT AGA (SEQ ID NO:82) | SAI4IC; |
| AACCUAGUUU CUUUAAAACU AGA (SEQ ID NO:83) | SAI4ICR; |
| UCUAGUUUUA AAGAAACUAG GUU (SEQ ID NO:84) | SAI4R; |
| GTGAGAGATC ACCAAGTAAT GCA (SEQ ID NO:57) | SPI1; |
| TGCATTACTT GGTGATCTCT CAC (SEQ ID NO:58) | SPI1IC; |
| UGCAUUACUU GGUGAUCUCU CAC (SEQ ID NO:59) | SPI1ICR; |
| GUGAGAGAUC ACCAAGUAAU GCA (SEQ ID NO:60) | SPI1R; |
| AGGAACTGCG CATTGGTCTT (SEQ ID NO:61) | SPI2; |
| AAGACCAATG CGCAGTTCCT (SEQ ID NO:62) | SPI2IC; |
| AAGACCAAUG CGCAGUUCCU (SEQ ID NO:63) | SPI2ICR; |
| AGGAACUGCG CAUUGGUCUU (SEQ ID NO:64) | SPI2R; |

```
GAGTTTATGA CTGAAAGGTC AGAA (SEQ ID NO:65)        SPI3;

TTCTGACCTT TCAGTCATAA ACTC (SEQ ID NO:66)        SPI3IC;

UUCUGACCUU UCAGUCAUAA ACUC (SEQ ID NO:67)        SPI3ICR;
                                                 or
GAGUUUAUGA CUGAAAGGUC AGAA (SEQ ID NO:68)        SPI3R.
```

7. The method of claim 1 wherein the microorganism is selected from the group consisting of *Neisseria gonorrhoeae, Neisseria meningitidis, Haemophilus ducreyi, Branhamella catarrhalis, Bordetella pertussis, Haemophilus influenzae, Streptococcus pneumoniae, Streptococcus agalactiae, Campylobacter jejuni, Campylobacter coli,* and a combination thereof.

8. The method of claim 1, wherein the transcribed spacer region between the 16S and 23S rRNA gene has any of the sequences SEQ ID NO:85, 86, 87, 89, 90, 91, 93, 94, 95, 96, 97, or 98.

9. A kit for an in vitro detection of a microorganism in a biological sample, the kit comprising:
(a) at least one nucleic acid probe consisting of a sequence from a transcribed spacer region between the 16S and 23S rRNA genes of a prokaryotic microorganism and comprising about 15 to about 100 continguous nucleotides from a transcribed spacer region between 16S and 23S rRNA genes of a prokaryotic microorganism, or a variant of the nucleic acid comprising up to 3 mismatches in a 15 residue nucleic acid and up to 7 mismatches in a 100 or more residue nucleic acid, wherein the probe specifically detects species of the prokaryotic microorganism and wherein said probe does not include sequences of a tRNA gene;
(b) a hybridization buffer, or components for producing the hybridization buffer, the hybridization buffer being effective for forming solution in which a nucleic acid from the microorganism can hybridize with the nucleic acid probe; and
(c) reagents for detecting hybrids formed between the nucleic acid from the microorganism and the nucleic acid probe.

10. The kit of claim 9, further comprising:
(a) at least two primers, wherein a first primer is complementary to a 5' flanking region of a spacer region between the 16S and 23S rRNA genes of a prokaryotic microorganism; and a second primer is a complementary to a 3' flanking region of the spacer region of the prokaryotic microorganism: and
(b) an amplification buffer, or components of the amplification buffer, the amplification buffer being effective for forming a solution for an amplification reaction.

11. The kit according to claim 10, wherein the at least two primers hybridize to a conserved region of the 3-end and the 5'-end of the 16S and 23S genes respectively, of the prokaryotic microorganisms to be detected.

12. The kit according to claim 10, wherein the at least two primers have the following sequences SEQ ID NO:99 and 100, or SEQ ID NO:101 and 102.

13. The kit of claim 9, wherein the hybridization buffer comprises about 3×SSC (wherein 1×SSC is 0.15 M NaCl, 0.015 M sodium citrate, pH 7.0), about 25 mM of phosphate buffer pH 7.1. and 20% deionized formamide, 0.02% Ficoll, 0.02% bovine serum albumin, 0.02% polyvinylpyrrolidone and about 0.1 mg/ml sheared denatured salmon sperm DNA.

14. The kit of claim 9, wherein the sequence of the probe comprises a sequence of:

```
CGATGCGTCG TTATTCTACT TCGC  (SEQ ID NO:1)            NGI1;

GCGAAGTAGA ATAACGACGC ATCG  (SEQ ID NO:2)            NGI1IC;

GCGAAGUAGA AUAACGACGC AUCG  (SEQ ID NO:3)            NGI1ICR;

CGAUGCGUCG UUAUUCUACU UCGC  (SEQ ID NO:4)            NGI1R;

TTCGTTTACC TACCCGTTGA CTAAGTAAGC AAAC  (SEQ ID NO:5) NGI2;

GTTTGCTTAC TTAGTCAACG GGTAGGTAAA CGAA  (SEQ ID NO:6) NGI2IC;

GUUUGCUUAC UUAGUCAACG GGUAGGUAAA CGAA  (SEQ ID NO:7) NGI2ICR;

UUGGUUUACC UACCCGUUGA CUAAGUAAGC AAAC  (SEQ ID NO:8) NGI2R;

GGTCAAGTGT GACGTCGCCC TG    (SEQ ID NO:9)            NMI1;

CAGGGCGACG TCACACTTGA CC    (SEQ ID NO:10)           NMI1IC;

CAGGGCGACG UCACACUUGA CC    (SEQ ID NO:11)           NMI1ICR;

GGUCAAGUGU GACGUCGCCC UG    (SEQ ID NO:12)           NMI1R;

GTTCTTGGTC AAGTGTGACG TC    (SEQ ID NO:13)           NMI2;

GACGTCACAC TTGACCAAGA AC    (SEQ ID NO:14)           NMI2IC;

GACGUCACAC UUGACCAAGA AC    (SEQ ID NO:15)           NMI2ICR;
```

| | |
|---|---|
| GUUCUUGGUC AAGUGUGACG UC (SEQ ID NO:16) | NMI2R; |
| GCGTTCGTTA TAGCTATCTA CTGTGC (SEQ ID NO:17) | NMI3; |
| GCACAGTAGA TAGCTATAAC GAACGC (SEQ ID NO:18) | NNI3IC; |
| GCACAGUAGA UAGCUAUAAC GAACGC (SEQ ID NO:19) | NMI3ICR; |
| GCGUUCGUUA UAGCUAUCUA CUGUGC (SEQ ID NO:20) | NMI3R; |
| TGCGTTCGAT ATTGCTATCT ACTGTGCA (SEQ ID NO:21) | NMI4; |
| TGCACAGTAG ATAGCAATAT CGAACGCA (SEQ ID NO:22) | NMI4IC; |
| UGCACAGUAG AUAGCAAUAU CGAACGCA (SEQ ID NO:23) | NMI4ICR; |
| UGCGUUCGAU AUUGCUAUCU ACUGUGCA (SEQ ID NO:24) | NMI4R; |
| TTTTGTTCTTGGTCAAGTGTGACGTCGCCCTGAATGGATTCTGTTCCATT (SEQ ID NO:25) | NMI5; |
| AATGGAACAGAATCCATTCAGGGCGACGTCACACTTGACCAAGAACAAAA (SEQ ID NO:26) | NMI5C; |
| AAUGGAACAGAAUCCAUUCAGGGCGACGUCACACUUGACCAAGAACAAAA (SEQ ID NO:27) | NMI5ICR; |
| UUUUGUUCUUGGUCAAGUGUGACGUCGCCCUGAAUGGAUUCUGUUCCAUU (SEQ ID NO:28) | NMI5R; |
| TTTGCCTAAC ATTCCGTTGA CTAGAACATC AGAC (SEQ ID NO:29) | NMI6; |
| GTCTGATGTT CTAGTCAACG GAATGTTAGG CAAA (SEQ ID NO:30) | NMI6IC; |
| GUCUGAUGUU CUAGUCAACG GAAUGUUAGG CAAA (SEQ ID NO:31) | NMI6ICR; |
| UUUGCCUAAC AUUCCGUUGA CUAGAACAUC AGAC (SEQ ID NO:32) | NMI6R; |
| TTATTATGCG CGAGGCATAT TG (SEQ ID NO:41) | HDI1; |
| CAATATGCCT CGCGCATAAT AA (SEQ ID NO:42) | HDI1IC; |
| CAAUAUGCCU CGCGCAUAAU AA (SEQ ID NO:43) | HDI1ICR; |
| UUAUUAUGCG CGAGGCAUAU UG (SEQ ID NO:44) | HDI1R; |
| TTAAACATCT TACCAAAG (SEQ ID NO:33) | BCI1; |
| CTTTGGTAAG ATGTTTAA (SEQ ID NO:34) | BCI1IC; |
| CUUUGGUAAG AUGUUUAA (SEQ ID NO:35) | BCI1ICR; |
| UUAAACAUCU UACCAAAG (SEQ ID NO:36) | BCI1R; |
| TTGATGTTTA AACTTGCTTG GTGGA (SEQ ID NO:37) | BCI2; |
| TCCACCAAGC AAGTTTAAAC ATCAA (SEQ ID NO:38) | BCI2IC; |
| UCCACCAAGC AAGUUUAAAC AUCAA (SEQ ID NO:39) | BCI2ICR; |
| UUGAUGUUUA AACUUGCUUG GUGGA (SEQ ID NO:40) | BCI2R; |
| CCACACCCAT CCTCTGGACA GGCTT (SEQ ID NO:53) | BPI1; |
| AAGCCTGTCC AGAGGATGGG TGTGG (SEQ ID NO:54) | BPI1IC; |
| AAGCCUGUCC AGAGGAUGGG UGUGG (SEQ ID NO:55) | BPI1ICR; |
| CCACACCCAU CCUCUGGACA GGCUU (SEQ ID NO:56) | BPI1R; |
| ACGCATCAAA TTGACCGCAC TT (SEQ ID NO:45) | HII1; |
| AAGTGCGGTC AATTTGATGC GT (SEQ ID NO:46) | HII1IC; |
| AAGUGGGGUC AAUUUGAUGC GU (SEQ ID NO:47) | HII1ICR; |
| ACGCAUCAAA UUGACCGCAC UU (SEQ ID NO:48) | HII1R; |
| ACTTTGAAGT GAAAACTTAA AG (SEQ ID NO:49) | HII2; |
| CTTTAAGTTT TCACTTCAAA GT (SEQ ID NO:50) | HII2IC; |
| CUUUAAGUUU UCACUUCAAA GU (SEQ ID NO:51) | HII2ICR; |

-continued

| | |
|---|---|
| ACUUUGAAGU GAAAACUUAA AG (SEQ ID NO:52) | HII2R; |
| AATCGAAAGG TTCAAATTGT T (SEQ ID NO:69) | SAI1; |
| AACAATTTGA ACCTTTCGAT T (SEQ ID NO:70) | SAI1IC; |
| AACAAUUUGA ACCUUUCGAU U (SEQ ID NO:71) | SAI1ICR; |
| AAUCGAAAGG UUCAAAUUGU U (SEQ ID NO:72) | SAI1R; |
| GGAAACCTGC CATTTGCGTC TT (SEQ ID NO:73) | SAI2; |
| AAGACGCAAA TGGCAGGTTT CC (SEQ ID NO:74) | SAI2IC; |
| AAGACGCAAA UGGCAGGUUU CC (SEQ ID NO:75) | SAI2ICR; |
| GGAAACCUGC CAUUUGCGUC UU (SEQ ID NO:76) | SAI2R; |
| TCCACGATCT AGAAATAGAT TGTAGAA (SEQ ID NO:77) | SAI3; |
| TTCTACAATC TATTTCTAGA TCGTGGA (SEQ ID NO:78) | SAI3IC; |
| UUCUACAAUC UAUUUCUAGA UCGUGGA (SEQ ID NO:79) | SAI3ICR; |
| UCCACGAUCU AGAAAUAGAU UGUAGAA (SEQ ID NO:80) | SAI3R; |
| TCTAGTTTTA AAGAAACTAG GTT (SEQ ID NO:81) | SAI4; |
| AACCTAGTTT CTTTAAAACT AGA (SEQ ID NO:82) | SAI4IC; |
| AACCUAGUUU CUUUAAAACU AGA (SEQ ID NO:83) | SAI4ICR; |
| UCUAGUUUUA AAGAAACUAG GUU (SEQ ID NO:84) | SAI4R; |
| GTGAGAGATC ACCAAGTAAT GCA (SEQ ID NO:57) | SPI1; |
| TGCATTACTT GGTGATCTCT CAC (SEQ ID NO:58) | SPI1IC; |
| UGCAUUACUU GGUGAUCUCU CAC (SEQ ID NO:59) | SPI1ICR; |
| GUGAGAGAUC ACCAAGUAAU GCA (SEQ ID NO:60) | SPI1R; |
| AGGAACTGCG CATTGGTCTT (SEQ ID NO:61) | SPI2; |
| AAGACCAATG CGCAGTTCCT (SEQ ID NO:62) | SPI2IC; |
| AAGACCAAUG CGCAGUUCCU (SEQ ID NO:63) | SPI2ICR; |
| AGGAACUGCG CAUUGGUCUU (SEQ ID NO:64) | SPI2R; |
| GAGTTTATGA CTGAAAGGTC AGAA (SEQ ID NO:65) | SPI3; |
| TTCTGACCTT TCAGTCATAA ACTC (SEQ ID NO:66) | SPI3IC; |
| UUCUGACCUU UCAGUCAUAA ACUC (SEQ ID NO:67) | SPI3ICR; or |
| GAGUUUAUGA CUGAAAGGUC AGAA (SEQ ID NO:68) | SPI3R. |

15. The kit of claim 9, wherein the microorganism is selected from the group consisting of Neisseria gonorrhoeae, Neisseria meningitidis, Haemophilus ducreyi, Branhamella catarrhalis, Bordetella pertussis, Haemophilus influenzae, Streptococcus pneumoniae, Streptococcus agalactiae, Campylobacter jejuni, Campylobacter coli, and a combination thereof.

16. The kit of claim 9, wherein the transcribed spacer region between the 16S and 23S rRNA gene has any of the sequences SEQ ID NO:85, 86, 87, 89, 90, 91, 93, 94, 95, 96, 97, or 98.

* * * * *

UNITED STATES PATENT AND TRADEMARK OFFICE
CERTIFICATE OF CORRECTION

PATENT NO. : 6,656,689 B2
DATED : December 2, 2003
INVENTOR(S) : Rossau et al.

It is certified that error appears in the above-identified patent and that said Letters Patent is hereby corrected as shown below:

Title page,
Item [*] Notice, "U.S.C. 154(b) by 11 days" should read -- U.S.C. 154(b) by 16 days --.

Column 9,
Line 35, "Group NM16" should read -- Group NM16: --

Column 10,
Line 46, "(SEQ ID NO: 35" should read -- (SEQ ID NO: 35) --

Column 12,
Line 36, "Group SPI2" should read -- Group SPI2: --
Line 44, "Group SPI3" should read -- Group SPI3: --

Column 103,
Line 56, "165 and 235" should read -- 16S and 23S --
Line 63, "gene: and" should read -- gene; and --

Column 106,
Line 11, "NMI1ICR" should read -- NMI1CR --
Line 18, "NNI3IC" should read -- NMI3IC --
Line 26, "NMI5C" should read -- NMI5IC --
Line 27, "NMI5ICR" should read --NMI5IC4 --

Column 107,
Line 11, "AAGUGGGGUC" should read -- AAGUGCGGUC --

Column 110,
Line 21, "microorganism:" should read -- microorganism; --
Line 26, "3-end" should read -- 3'-end --
Line 51, "NMI1ICR" should read -- NMI1CR --

Column 111,
Line 36, "AAGUGGGGUC" should read -- AAGUGCGGUC --

UNITED STATES PATENT AND TRADEMARK OFFICE
CERTIFICATE OF CORRECTION

PATENT NO. : 6,656,689 B2
DATED : December 2, 2003
INVENTOR(S) : Rossau et al.

It is certified that error appears in the above-identified patent and that said Letters Patent is hereby corrected as shown below:

<u>Column 112,</u>
Line 3, "NNI3IC" should read -- NMI3IC --
Line 11, "NMI5C" should read -- NMI5IC --
Line 12, "NMI5ICR" should read -- NMI5IC4 --

Signed and Sealed this

Twenty-seventh Day of April, 2004

JON W. DUDAS
*Acting Director of the United States Patent and Trademark Office*

SEQUENCE LISTING (1) GENERAL INFORMATION:

(iii) NUMBER OF SEQUENCES: 104

(2) INFORMATION FOR SEQ ID NO: 1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 1:

CGATGCTGCG TTATTCTACT TCGC                                    24

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 2:

GCGAAGTAGA ATAACGACGC ATCG                             24

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 3:

GCGAAGUAGA AUAACGACGC AUCG                             24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 4:

CGAUGCGUCG UUAUUCUACU UCGC                             24

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 5:

```
TTCGTTTACC TACCCGTTGA CTAAGTAAGC AAAC                              34
```

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 6:

```
GTTTGCTTAC TTAGTCAACG GGTAGGTAAA CGAA                              34
```

(2) INFORMATION FOR SEQ ID NO: 7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 7:

```
GUUUGCUUAC UUAGUCAACG GGUAGGUAAA CGAA                              34
```

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 8:

```
UUGGUUUACC UACCCGUUGA CUAAGUAAGC AAAC                              34
```

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 9:

GGTCAAGTGT GACGTCGCCC TG                                             22

(2) INFORMATION FOR SEQ ID NO: 10:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 10:

CAGGGCGACG TCACACTTGA CC                                             22

(2) INFORMATION FOR SEQ ID NO: 11:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

CAGGGCGACG UCACACUUGA CC                                             22

(2) INFORMATION FOR SEQ ID NO: 12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

GGUCAAGUGU GACGUCGCCC UG                                    22

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

GTTCTTGGTC AAGTGTGACG TC                                    22

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

GACGTCACAC TTGACCAAGA AC                                    22

(2) INFORMATION FOR SEQ ID NO: 15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 15:

GACGUCACAC UUGACCAAGA AC                                    22

(2) INFORMATION FOR SEQ ID NO: 16:

(i) SEQUENCE CHARACTERISTICS:
        (A) LENGTH: 22 base pairs (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

GUUCUUGGUC AAGUGUGACG UC                                            22

(2) INFORMATION FOR SEQ ID NO: 17:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

GCGTTCGTTA TAGCTATCTA CTGTGC                                        26

(2) INFORMATION FOR SEQ ID NO: 18:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

GCACAGTAGA TAGCTATAAC GAACGC                                        26

(2) INFORMATION FOR SEQ ID NO: 19:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

GCACAGUAGA UAGCUAUAAC GAACGC                                            26

(2) INFORMATION FOR SEQ ID NO: 20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

GCGUUCGUUA UAGCUAUCUA CUGUGC                                            26

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

TGCGTTCGAT ATTGCTATCT ACTGTGCA                                          28

(2) INFORMATION FOR SEQ ID NO: 22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

TGCACAGTAG ATAGCAATAT CGAACGCA                                          28

(2) INFORMATION FOR SEQ ID NO: 23:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

UGCACAGUAG AUAGCAAUAU CGAACGCA                                              28

(2) INFORMATION FOR SEQ ID NO: 24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

UGCGUUCGAU AUUGCUAUCU ACUGUGCA                                              28

(2) INFORMATION FOR SEQ ID NO: 25:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

TTTTGTTCTT GGTCAAGTGT GACGTCGCCC TGAATGGATT CTGTTCCATT                      50

(2) INFORMATION FOR SEQ ID NO: 26:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

AATGGAACAG AATCCATTCA GGGCGACGTC ACACTTGACC AAGAACAAAA                50

(2) INFORMATION FOR SEQ ID NO: 27:

(i) SEQUENCE CHARACTERISTICS:
             (A) LENGTH: 50 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 27:

AAUGGAACAG AAUCCAUUCA GGGCGACGUC ACACUUGACC AAGAACAAAA                50

(2) INFORMATION FOR SEQ ID NO: 28:

(i) SEQUENCE CHARACTERISTICS:
             (A) LENGTH: 50 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 28:

UUUUGUUCUU GGUCAAGUGU GACGUCGCCC UGAAUGGAUU CUGUUCCAUU                50

(2) INFORMATION FOR SEQ ID NO: 29:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 29:

TTTGCCTAAC ATTCCGTTGA CTAGAACATC AGAC                                 34

(2) INFORMATION FOR SEQ ID NO: 30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 30:

GTCTGATGTT CTAGTCAACG GAATGTTAGG CAAA          34

(2) INFORMATION FOR SEQ ID NO: 31:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 31:

GUCUGAUGUU CUAGUCAACG GAAUGUUAGG CAAA          34

(2) INFORMATION FOR SEQ ID NO: 32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 32:

UUUGCCUAAC AUUCCGUUGA CUAGAACAUC AGAC          34

(2) INFORMATION FOR SEQ ID NO: 33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear -continued (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 33:

TTAAACATCT TACCAAAG                                          18

(2) INFORMATION FOR SEQ ID NO: 34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 34:

CTTTGCTAAG ATGTTTAA                                          18

(2) INFORMATION FOR SEQ ID NO: 35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 35:

CUUUGGUAAG AUGUUUAA                                         18

(2) INFORMATION FOR SEQ ID NO: 36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 36:

UUAAACAUCU UACCAAAG                                                    18

(2) INFORMATION FOR SEQ ID NO: 37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 37:

TTGATGTTTA AACTTGCTTG GTGGA                                            25

(2) INFORMATION FOR SEQ ID NO: 38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 38:

TCCACCAAGC AAGTTTAAAC ATCAA                                            25

(2) INFORMATION FOR SEQ ID NO: 39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 39:

UCCACCAAGC AAGUUUAAAC AUCAA                                            25

(2) INFORMATION FOR SEQ ID NO: 40:

(i) SEQUENCE CHARACTERISTICS:
        (A) LENGTH: 25 base pairs
        (B) TYPE: nucleic acid

```
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 40:

UUGAUGUUUA AACUUGCUUG GUGGA                                              25

(2) INFORMATION FOR SEQ ID NO: 41:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 41:

TTATTATGCG CGAGGCATAT TG                                                 22

(2) INFORMATION FOR SEQ ID NO: 42:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 42:

CAATATGCCT CGCGCATAAT AA                                                 22

(2) INFORMATION FOR SEQ ID NO: 43:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>
```

(vi) ORIGINAL SOURCE:

(xi) SEQUENCE DESCRIPTION: SEQ ID NO: 43:

CAAUAUGCCU CGCGCAUAAU AA                                              22

(2) INFORMATION FOR SEQ ID NO: 44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 44:

UUAUUAUGCG CGAGGCAUAU UG                                              22

(2) INFORMATION FOR SEQ ID NO: 45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 45:

ACGCATCAAA TTGACCGCAC TT                                              22

(2) INFORMATION FOR SEQ ID NO: 46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 46:

AAGTGCGGTC AATTTGATGC GT                                              22

(2) INFORMATION FOR SEQ ID NO: 47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 47:

AAGUGCGGUC AAUUUGAUGC GU                                                    22

(2) INFORMATION FOR SEQ ID NO: 48:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 48:

ACGCAUCAAA UUGACCGCAC UU                                                    22

(2) INFORMATION FOR SEQ ID NO: 49:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 49:

ACTTTGAAGT GAAAACTTAA AG                                                    22

(2) INFORMATION FOR SEQ ID NO: 50:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 50:

CTTTAAGTTT TCACTTCAAA GT                                                     22

(2) INFORMATION FOR SEQ ID NO: 51:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 51:

CUUUAAGUUU UCACUUCAAA GU                                                     22

(2) INFORMATION FOR SEQ ID NO: 52:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 52:

ACUUUGAAGU GAAAACUUAA AG                                                     22

(2) INFORMATION FOR SEQ ID NO: 53:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 53:

CCACACCCAT CCTCTGGACA GGCTT                                                  25

(2) INFORMATION FOR SEQ ID NO: 54:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 54:

AAGCCTGTCC AGAGGATGGG TGTGG                                       25

(2) INFORMATION FOR SEQ ID NO: 55:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 55:

AAGCCUGUCC AGAGGAUGGG UGUGG                                       25

(2) INFORMATION FOR SEQ ID NO: 56:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 56:

CCACACCCAU CCUCUGGACA GGCUU                                       25

(2) INFORMATION FOR SEQ ID NO: 57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 57:

GTGAGAGATC ACCAAGTAAT GCA                                              23

(2) INFORMATION FOR SEQ ID NO: 58:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 58:

TGCATTACTT GGTGATCTCT CAC                                              23

(2) INFORMATION FOR SEQ ID NO: 59:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 59:

UGCAUUACUU GGUGAUCUCU CAC                                              23

(2) INFORMATION FOR SEQ ID NO: 60:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 60:

GUGAGAGAUC ACCAAGUAAU GCA                                        23

(2) INFORMATION FOR SEQ ID NO: 61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 61:

AGGAACTGCG CATTGGTCTT                                            20

(2) INFORMATION FOR SEQ ID NO: 62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 62:

AAGACCAATG CGCAGTTCCT                                            20

(2) INFORMATION FOR SEQ ID NO: 63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 63:

AAGACCAAUG CGCAGUUCCU                                            20

(2) INFORMATION FOR SEQ ID NO: 64:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 64:

AGGAACUGCG CAUUGGUCUU                                              20

(2) INFORMATION FOR SEQ ID NO: 65:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 65:

GAGTTTATGA CTGAAAGGTC AGAA                                         24

(2) INFORMATION FOR SEQ ID NO: 66:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 66:

TTCTGACCTT TCAGTCATAA ACTC                                         24

(2) INFORMATION FOR SEQ ID NO: 67:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 67:

UUCUGACCUU UCAGUCAUAA ACUC                                              24

(2) INFORMATION FOR SEQ ID NO: 68:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 68:

GAGUUUAUGA CUGAAAGGUC AGAA                                              24

(2) INFORMATION FOR SEQ ID NO: 69:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 69:

AATCGAAAGG TTCAAATTGT T                                                 21

(2) INFORMATION FOR SEQ ID NO: 70:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 70:

AACAATTTGA ACCTTTCGAT T                                                 21

(2) INFORMATION FOR SEQ ID NO: 71:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 71:

AACAAUUUGA ACCUUUCGAU U                                        21

(2) INFORMATION FOR SEQ ID NO: 72:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 72:

AAUCGAAAGG UUCAAAUUGU U                                        21

(2) INFORMATION FOR SEQ ID NO: 73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 73:

GGAAACCTGC CATTTGCGTC TT                                       22

(2) INFORMATION FOR SEQ ID NO: 74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 74:

AAGACGCAAA TGGCAGGTTT CC                                              22

(2) INFORMATION FOR SEQ ID NO: 75:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 75:

AAGACGCAAA UGGCAGGUUU CC                                              22

(2) INFORMATION FOR SEQ ID NO: 76:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 76:

GGAAACCUGC CAUUUGCGUC UU                                              22

(2) INFORMATION FOR SEQ ID NO: 77:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 77:

TCCACGATCT AGAAATAGAT TGTAGAA                                         27

(2) INFORMATION FOR SEQ ID NO: 78:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 78:

TTCTACAATC TATTTCTAGA TCGTGGA                          27

(2) INFORMATION FOR SEQ ID NO: 79:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 79:

UUCUACAAUC UAUUUCUAGA UCGUGGA                          27

(2) INFORMATION FOR SEQ ID NO: 80:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 80:

UCCACGAUCU AGAAAUAGAU UGUAGAA                          27

(2) INFORMATION FOR SEQ ID NO: 81:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 81:

TCTAGTTTTA AAGAAACTAG GTT                                                  23

(2) INFORMATION FOR SEQ ID NO: 82:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 82:

AACCTAGTTT CTTTAAAACT AGA                                                  23

(2) INFORMATION FOR SEQ ID NO: 83:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 83:

AACCUAGUUU CUUUAAAACU AGA                                                  23

(2) INFORMATION FOR SEQ ID NO: 84:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 84:

UCUAGUUUUA AAGAAACUAG GUU                                              23

(2) INFORMATION FOR SEQ ID NO: 85:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 85:

AGAGAAAGAA GGGGCTTTAG GCATTCACAC TTATCGGTAA ACTGAAAAGA TGCGGAAGAA      60

GCTTGAGTGA AGGCAAGGTT CGCTTAAGAA GGGAAACCGG GTTTGTAGCT CAGCTGGTTA     120

GAGCACACGC TTGATAAGCG TGAGGTCGGA GGTTCAAGTC CTCCCAGACC CACCAAGAAC     180

GGGGGCATAG CTCAGTTGGT AGAGCACCTG CTTTGCAAGC AGGGGGTCAT CGGTTCGATC     240

CCGTTTGCCT CCACCAAAAC TTTACAAATG AAAGCAAGTT TGCTGTTTTT AGCAGCTTAT     300

TTTGATTTGC GAAGTAGAAT AACGACGCAT CGATCTTTAA CAAATTGGAA AGCCGAAATC     360

AACAAACAAA GACAATGAGT TTGTTTTGAT TTTTTATTCT TTGCAAAGGA TAAAAAATCT     420

CTCGCAAGAG AAAAGAAAAC AAACATAGTA TTTGGGTGAT GATTGTATCG ACTTAATCCT     480

GAAACACAAA AGGCAGGATT AAGACACAAC AAAGCAGTAA GCTTTATCAA AGTAGGGATT     540

TCAAGTTTGC TTACTTAGTC AACGGGTAGG TAAACGAAGT CAAAGAAGTT CTTGAAATGA     600

TAG                                                                  603

(2) INFORMATION FOR SEQ ID NO: 86:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 86:

AGAGAAAGAA GGGGCTTTAG GCATTCACAC TTATCGGTAA ACTGAAAAGA TGCGGAAGAA      60

GCTTGAGTGA AGGCAAGGTT CGCTTAAGAA GGGAAACCGG GTTTGTAGCT CAGCTGGTTA     120

GAGCACACGC TTGATAAGCG TGAGGTCGGA GGTTCAAGTC CTCCCAGACC CACCAAGAAC     180

GGGGGCATAG CTCAGTTGGT AGAGCACCTG CTTTGCAAGC AGGGGGTCAT CGGTTCGATC     240

CCGTTTGCCT CCACCAAAAC TTTACAAATG AAAGCAAGTT TGCTGTTTTT AGCAGCTTAT     300

TTTGATTTGC GAAGTAGAAT AACGACGCAT CGATCTTTAA CAAATTGGAA AGCCGAAATC     360

AACAAACAAA GACAATGAGT TTGTTTTGAT TTTTTATTCT TTGCAAAGGA TAAAAAATCT     420

```
CTCGCAAGAG AAAAGAAAAC AAACATAGTA TTTGGGTGAT GATTGTATCG ACTTAATCCT        480

GAAACACAAA AGGCAGGATT AAGACACAAC AAAGCAGTAA GCTTTATCAA AGTAGGGATT        540

TCAAGTTTGC TTACTTAGTC AACGGGTAGG TAAACGAAGT CAAAGAAGTT CTTGAAATGA        600

TAG                                                                     603
```

(2) INFORMATION FOR SEQ ID NO: 87:

(i) SEQUENCE CHARACTERISTICS:
        (A) LENGTH: 582 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 87:

```
AAGAGCTTGA GTGCTCGTGT CAAGTGTCCA CGCTTATCGG TTGTTGTTAT ATAGCTGCTG         60

GATCGGTGGC TGCTGATCCG AGAGAGAAAG GTTTCGCGGG TCTGTAGCTC AGTCGGTTAG        120

AGCACCGTCT TGATAAGGCG GGGGTCGTTG GTTCGAATCC AACCAGACCC ACCAAGGTTT        180

CCTGAGAGGG AAATGGGGGT GTAGCTCAGC TGGGAGAGCG CCTGCTTTGC AAGCAGGATG        240

TCATCGGTTC GATCCCGTTC ACCTCCACCA AAGCCTGTCC AGAGGATGGG TGTGGNNNGA        300

GACCAGAAGG CGAGAGAGCA ACGTTAGTGC TGCGAGTCAG TGTTAAGCGT TGGGTTTTGG        360

CCGACAGCTA TATATGTTCT TTAACAATTT GGAAGAAGCA CAACGTAAAG TGTTCGTTTA        420

GTAGTCGGCG CGAGTCGATG AAGACGGATA CGGGTTGTGA TTGCATGATT TTGTTCCAAG        480

TCTCAAGAAC TGGCTGGGCG GCCAAGCGTT TGGTCAGATG CTTTGAACTT ATGAACGGCA        540

CAAGCGCGAA TGAACAGCAC CTATAAGACT TTAGTGTTAT AG                          582
```

(2) INFORMATION FOR SEQ ID NO: 88:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 88:

```
AAGAGCTTGA GTGCTCGTGT CAAGTGTCCA CGCTTATCGG TTGTTGTTAT ATAGCTGCTG         60

GATCGGTGGC TGCTGATCCG AGAGAGAAAG GTTTCGCGGG TCTGTAGCTC AGTCGGTTAG        120

AGCACCGTCT TGATAAGGCG GGGGTCGTTG GTTCGAATCC AACCAGACCC ACCAAGGTTT        180

CCTGAGAGGG AAATGGGGGT GTAGCTCAGC TGGGAGAGCG CCTGCTTTGC AAGCAGGATG        240
```

```
TCATCGGTTC GATCCCGTTC ACCTCCACCA GAGCCCGTCT TGAAGATGGG AGCGGGTTGG      300

CAGGCGAGAC CAGGAAGGCG AGAGAGCAAC GTTAGTGCTG CGAGTCAGTG TTAAGCGTTG      360

GGTTTTGGCC GACAGCTATA TATGTTCTTT AACAATTTGG AAGAAGCACA ACGTAAAGTG      420

TTCGTTTAGT AGTCGACGCG AGTCGATGAA GACGGATACG GGTTGTGATT GCATGATTTT      480

GTTCCAAGTC TCAAGAACTG GCTGGGCGGC CAAGCGTTTG GTCAGATGCT TTGAACTTAT      540

GAACGGCACA AGCGCGAATG AACAGCACCT ATAAGACTTT AGTGTTATAG                 590
```

(2) INFORMATION FOR SEQ ID NO: 89:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 89:

```
AGAGAAAGAA GAGGCTTTAG GCATTCACAC TTATCGGTAA ACTGAAAAAG ATGCGGAAGA       60

AGCTTGAGTG AAGGCAAGAT TCGCTTAAGA AGAGAATCCG GGTTTGTAGC AGAGCACACG      120

CTTGATAAGC GTGGGGTCGG AGGTTCAAGT CCTCCCAGAC CCACCAAGAA CGGGGGGCAT      180

AGCTCAGTTG GTAGAGCACC TGCTTTGCAA GCAGGGGTC ATCGGTTCGA TCCCGTTTGC       240

CTCCACCAAT ACTGTACAAA TCAAAACGGA AGAATGGAAC AGAATCCATT CAGGGCGACG      300

TCACACTTGA CCAAGAACAA AATGCTGATA TAATAATCAG CTCGTTTTGA TTTGCACAGT      360

AGATAGCAAT ATCGAACGCA TCGATCTTTA ACAAATTGGA AAGCCGAAAT CAACAAACAA      420

AGACAAAGCG TTTGTTTTGA TTTTTTATTC TTTGCAAAGG ATAAAAAATC GCTCACAAGA      480

GAAAAGAAAA CAAACACAGT ATTTGGGTGA TGATTGTATC GACTTAACCC TGAAACACAA      540

AAGGCAGGAT TAAGACACAA CAAAGCAGTA AGCTTTATCA AAGTAGGAAA TTCAAGTCTG      600

ATGTTCTAGT CAACGGAATG TTAGGCAAAG TCAAAGAAGT TCTTGAAATG ATAG           654
```

(2) INFORMATION FOR SEQ ID NO: 90:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 90:

```
ACGAAGTTAT CTGATTGGCA AGAATCCACA ACAAGTTGTT CTTTGGTAAG ATGTTTAAAA       60

ACGGGTCTAT AGCTCAGTTG GTTAGAGCAC CGTGTTGATA ACGCGGGGGT CATAAGTTCA      120
```

```
AGTCTTATTA GACCCACCAT TTTGGGGCCA TAGCTCAGTT GGTAGAGCGC CTGCCTTGCA      180

CGCAGGAGGT CAGGAGTTCG ACTCTCCTTG GCTCCACCAA GCAAGTTTAA ACATCAAAGC      240

ATACATAAGC AATTTAAATA AGATTTCTTA TTTATGCTTT TATTTTATAA ACTGACGAAG      300

TTTATAACAT TATTTAACAA CATAGTATGA GTCTGGGTTA ATTATTTAAT TCCAACAAAT      360

AATTAACCTG GTGTTTGTAC CCAATACAAA CACCAAAAAA GTAAAGAGAA CTGAATCAAG      420

CGTAAACATA GGTGAATCGT TACACATTAC CCATACACAC CAAAGACTTC CTAGAAGTCA      480

GACTACTTGG GGTTGTAT                                                   498
```

(2) INFORMATION FOR SEQ ID NO: 91:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 91:

```
CCAAAATAAA GACATCACAA GTACTCACAC AGATTGTTTG ATTGTTTTAG ACAAGTCGGA       60

ATACATCTTT AAATGTTGTC CCCATCTGTC TAGAGGCCTA GGACATCGCC CTTTCACGGC      120

GGTAACCGGG GTTCGAANCC CCGTGGACGC CATCTAAAGA TGATTTTTAT TGTCTTATGT      180

TCTTTAAAAA AATAGAAACA AGCTGAAAAC TGAGAGATTT CTAAAGTAG AAAGTCTGAG       240

TAATCTAAAA TCTTAGCTGA ACAAAAGCAG CTAAGTGTTT AGTCTAAATC ATTAACCACA      300

AGTATATCAA TATGCCTCGC GCATAATAAA ATACTTGAGG TTGTAT                    346
```

(2) INFORMATION FOR SEQ ID NO: 92:

(i) SEQUENCE CHARACTERISTICS:
        (A) LENGTH: 549 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 92:

```
ACGAGATTAT CTGATTGGCA AGAATCCACA ACAAGTTGTT CTTAGTAGTG TAAGTTAAAT       60

TGGGTCTATA GCTCAGTTGG TTAGAGCACC GCCTTGATAA GGCGGGGGTC ATAAGTTCAA      120

GTCTTATTAG ACCCACCATT TGGGGTTAT AGCTCAGTTG GTAGAGCGCC TGCCTTGCAC       180

GCAGGAGGTC AGGAGTTCGA CTCTCCTTAA CTCCACCACT TACAATAAAT GAGAACTAAG      240

CAATCAAATT AGATAACATA AAATTAGATT TCTTACTTCT ACTTTATGTA GATGACTTAC      300
```

```
AATTAACTGA TGAAGTTAAT TTCAATTATT TAACAACGTA TATATGAGTC TGGGTTAATT        360

ATTTAATTCC AACAAATAAT TAACCATTCC GTCATACTCC ACATCAAGCA TATAAAGTTA        420

AAACTTTTAG TATTGATGAT GATCGGATAA AGTAAAGAGA ACTGAATCAA GCGTAAACAT        480

AGGTGAATCG TTACACATTA CCCATACACA CCAAAGACTT CCTAGAAGTC AGACTACTTG        540

GGGTTGTAT                                                                549

(2) INFORMATION FOR SEQ ID NO: 93:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 93:

CTGAAGACGA GAGACAGCGA GTGCTCACAC AGATTGGCTG ATAGTTGTAG ACAAGATTAA         60

AAACGAAGCG AAAGCAACGT TGAAAAATAA ACGTTAAAAG ATAAAAAGAA AATAGAGTAT        120

CTTTAATTGA TGTCCCCATC GTCTAGAGGC CTAGGACATC GCCCTTTCAC GGCGGTAACC        180

GGGGTTCGAA TCCCCGTGGG ACGCCAATTA AAGATAACTT TATTAGATTG TCTTACTGTT        240

CTTTAAAAAA TTGGAAACAA GCTGAAAACA AGAGATTTTC GAGAGAAAGT CTGAGTAGGC        300

AAGATAGGAA AGTGAGAGGA GGGAACTGAA AAGGGAACTC TAAAAACAAA ACCTGTTTTG        360

CATAAAATCT TGATTGAACA AAAGCAATCA AGTGTTTAGT TGAATGAAAA TACGCATCAA        420

ATTGACCGCA CTTTGAAGTG AAAACTTAAA GTGATTGAAA ACATTTGAGG TGAT             474

(2) INFORMATION FOR SEQ ID NO: 94:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 94:

CCCAAGACGA GAGACAGCGA GTGCTCACAC AGATTGGCTG ATAGTTGTAG ACAAGATTAA         60

AAACGAAGCG AAAGCAACGT TGAAAAATAA ACGTTAAAAG ATAAAAAGAA AATAGAGTAT        120

CTTTAATTGA TGTCCCCATC GTCTAGAGGC CTAGGACATC GCCCTTTCAC GGCGGTAACC        180

GGGGTTCGAA TCCCCGTGGG ACGCCANNNN NNNNNNNNTT TATTAGATTG TCTTACTGTT        240

CTTTAAAAAA TTGGAAACAA GCTGAAAACA AGAGATTTTC GAGAGAAAGT CTGAGTAGGC        300

AAGACAGGAA AGTGAAAAGA GGGAACTGAG AAGGAAACTC TAAAAACAAA CCTGTTTTGT        360
```

| | |
|---|---|
| AAAAAAATCT TGATTGAACA AAAGTAATCA AGTGTTTAGT TGAATTAATG AGGCTGAAAG | 420 |
| TGCAGTCAAA GTACGGTATC TATTTTATAT TGAGTTTTGA AAACATTTGA NNNNNN | 476 |

(2) INFORMATION FOR SEQ ID NO: 95:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 95:

| | |
|---|---|
| AAGGATAAGG AACTGCGCAT TGGTCTTGTT TAGTCTTGAG AGGTCTTGTG GGGCCTTAGC | 60 |
| TCAGCTGGGA GAGCGCCTGC TTTGCACGCA GGAGGTCAGC GGTTCGATCC CGCTAGGCTC | 120 |
| CATTGGTGAG AGATCACCAA GTAATGCACA TTGAAAATTG AATATCTATA TCAAATAGTA | 180 |
| ACAAGAAAAT AAACCGAAAA CGCTGTAGTA TTAATAAGAG TTTATGACTG AAAGGTCAGA | 240 |
| AAATAA | 246 |

(2) INFORMATION FOR SEQ ID NO: 96:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 96:

| | |
|---|---|
| AAGGATAAGG AAACCTGCCA TTTGCGTCTT GTTTAGTTTT GAGAGGTCTT GTGGGGCCTT | 60 |
| AGCTCAGCTG GGAGAGCGCC TGCTTTGCAC GCAGGAGGTC AGCGGTTCGA TCCCGCTAGG | 120 |
| CTCCATTGAA TCGAAAGGTT CAAATTGTTC ATTGAAAATT GAATATCTAT ATCAAATTCC | 180 |
| ACGATCTAGA AATAGATTGT AGAAAGTAAC AAGAAAATAA ACCGAAAACG CTGTGAATAT | 240 |
| TTAATGAGTT TTCTAGTTTT AAAGAAACTA GGTTAATAA | 279 |

(2) INFORMATION FOR SEQ ID NO: 97:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 97:

```
TAAAATCTAA AGCAAGTATA TAAAGTAGAT TAAATATAAA ATACAAACTC TATACTTAGA      60
TTTATTTTTA TCTTTAACTA TAAAAGAATA TACTTTAATA AATATAAATA ACATATACAT     120
TATGTATTTA TATTTATAAT GAGATTATTT AATATATATG CTTCCTTTAG GTTTTAAACC     180
TAAATGTTCT TTTTAATTAT CATTGTTAAG AGTCACAAGC AAGTTTTAAT AAAAACAATT     240
TTACAGGACT TGTTAAAGGA TAAAACCTAT TTATCTTTTC TTTGGTTTAA CTTATATCTT     300
TTAATTATCT TTATTTCTAT AATAAAGAGA ATATTAGATT TAAGATTTAT AAATTAAAGA     360
CAAGTTTCAA ACTCACAGCT TAGTTGAGAC TAAATCATTT AGTTTTATAT TAAGTGTTTG     420
AATGCTTTCC GTCTTAAGAT AAAGAAGTCT TATCATAAAA ACTTTAACAA GGAAGTGATG     480
CGTTTTAGAA TCAATAATAA AAGGTAAAAA A                                    511
```

(2) INFORMATION FOR SEQ ID NO: 98:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 98:

```
TAAAATCTAA AGCAAGTATA TAAAGTAGAT TAAATATAAA ATACAAACTC TATACTTAGA      60
TTTATTTTTA TCTTTAACTA TAAAAGAATA TACTTTAATA AATATAAATA ACATATACAT     120
TATGTATTTA TATTTATAAT GAGATTATTT AATATATATG CTTCCTTTAG GTTTTAAACC     180
TAAATGTTCT TTTTAATTAT CATTGTTAAG AGTCACAAGC AAGTTTTAAT AAAAACAATT     240
TTACAGGACT TGTTAAAGGA TAAAACCTAT TTATCTTTTC TTTGGTTTAA CTTATATCTT     300
TTAATTATCT TTATTTCTAT AATAAAGAGA ATATTAGATT TAAGATTTAT AAATTAAAGA     360
CAAGTTTCAA ACTCACAGCT TAGTTGAGAC TAAATCATTT AGTTTTATAT TAAGTGTTTG     420
AATGCTTTCC GTCTTAAGAT AAAGAAGTCT TATCATAAAA ACTTTAACAA GGAAGTGATG     480
CGTTTTAGAA TCAATAATAA AAGGTAAAAA A                                    511
```

(2) INFORMATION FOR SEQ ID NO: 99:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 99:

TGGCTCAGAT TGAACGCTGG CGGC                                              24

(2) INFORMATION FOR SEQ ID NO: 100:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 100:

CCTTTCCCTC ACGGTACTGG T                                                 21

(2) INFORMATION FOR SEQ ID NO: 101:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 101:

TGGGTGAAGT CGTAACAAGG TA                                                22

(2) INFORMATION FOR SEQ ID NO: 102:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 102:

CACGTCCTTC GTCGCCT                                                      17

(2) INFORMATION FOR SEQ ID NO: 103:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 103:

TGGGTGAAGT CGTAACAAGG TA                                                22

(2) INFORMATION FOR SEQ ID NO: 104:

(i) SEQUENCE CHARACTERISTICS:
(A) LENGTH: 17 base pairs
(B) TYPE: nucleic acid
(C) STRANDEDNESS: both
(D) TOPOLOGY: both (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 104:

CACGTCCTTC GTCGCCT                                                      17